(12) United States Patent
Dehmlow et al.

(10) Patent No.: US 7,732,452 B2
(45) Date of Patent: Jun. 8, 2010

(54) THIOPHENE DERIVATIVES WHICH ARE HM74A AGONISTS

(75) Inventors: Henrietta Dehmlow, Grenzach-Wyhlen (DE); Uwe Grether, Efringen-Kirchen (DE); Nicole A. Kratochwil, Sool (CH); Robert Narquizian, St. Louis (FR); Constantinos G. Panousis, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/638,220

(22) Filed: Dec. 13, 2006

(65) Prior Publication Data
US 2007/0161650 A1    Jul. 12, 2007

Related U.S. Application Data

(63) Continuation-in-part of application No. 11/524,145, filed on Sep. 20, 2006, now abandoned.

(30) Foreign Application Priority Data

Jun. 27, 2005 (EP) .................................. 05108907

(51) Int. Cl.
*A61K 31/497* (2006.01)
*C07D 409/02* (2006.01)

(52) U.S. Cl. .................. 514/255.05; 514/269; 514/342; 514/447; 544/314; 544/405; 546/281.4; 549/69; 549/71

(58) Field of Classification Search ........................ None
See application file for complete search history.

(56) References Cited

U.S. PATENT DOCUMENTS 6,362,210 B1 * 3/2002 Hauel et al. .................. 514/396
2004/0048802 A1 * 3/2004 Ripka et al. .................... 514/18

FOREIGN PATENT DOCUMENTS

DE            3305866        *  8/1984

WO    WO 2005042488 A1 *  5/2005

OTHER PUBLICATIONS

Binder et al., Arch der Pharmazie, 1981, vol. 4, No. 6, pp. 557-564.*
Jin et al Arterioscler. Thromb. Vasc. Biol. 1997, 17, 2020-2028.
Carlson et al. J. Intern. Med. 1989, 226, 271-6.
Grundy et al. Arch. Intern. Med. 2002, 162, 1568-76.
Wise et al. J. Biol. Chem. 2003, 278 (11) 9869-9874.
Soga et al Biochem Biophys Res Commun 2003 303 (1) 364-369.
Tunaru et al Nature Medicine 2003, (3) 352-255.
Z.J. Song et al., Organic Letters, 4, 1623; 2002.
R.C. Larock et al., Organic Letters, 6, 99; 2004.
J.F. Hartwig et al., J. Am. Chem. Soc., 121, 3224; 1999.
O. Mitsunobu, *Synthesis* 1981, 1.
Suzuki, A. *Acc. Chem. Res.* 1982, 15, 178.
Scott, W. J.; Crisp, G. T.; Stille, J. K. *J. Am. Chem. Soc*. 1984, 106, 4630.
Heck, R. F. *Organic React.* 1982, 27, 345.

* cited by examiner

*Primary Examiner*—Zinna N Davis
(74) *Attorney, Agent, or Firm*—George W. Johnston; Dennis P. Tramaloni; Samuel H. Megerditchian

(57) ABSTRACT

The invention is concerned with novel substituted thiophene derivatives of formula (I)

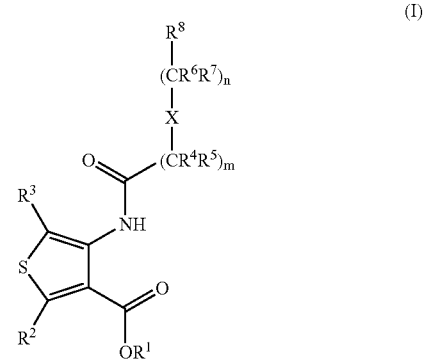

wherein $R^1$ to $R^8$, X, m and n are as defined in the description and in the claims, as well as physiologically acceptable salts and esters thereof. These compounds are HM74A agonists and can be used as medicaments.

26 Claims, No Drawings

THIOPHENE DERIVATIVES WHICH ARE HM74A AGONISTS

PRIORITY TO RELATED APPLICATIONS

This application is a Continuation-in-Part of U.S. application Ser. No. 11/524,145, filed Sep. 20, 2006, now abandoned; which claims the benefit of European Application No. 05108907.6, filed Sep. 27, 2005. The entire contents of the above-identified applications are hereby incorporated by reference.

FIELD OF THE INVENTION

The invention is concerned with novel substituted thiophene derivatives of the formula (I)

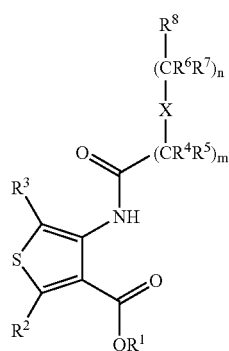

and pharmaceutically acceptable salts and pharmaceutically acceptable esters thereof.

Further, the invention is concerned with a process for the manufacture of the above compounds, pharmaceutical preparations which contain such compounds as well as the use of these compounds for the production of pharmaceutical preparations.

All documents cited or relied upon below are expressly incorporated herein by reference.

BACKGROUND

Coronary heart disease (CHD) remains the leading cause of death in Western countries. In the United States 13.2 million or 4.85% of the population is affected, with 1.2 million new or recurrent attacks and around 500 thousand deaths per year (American Heart Association, Statistics for 2001). The disease is influenced by several well-established risk factors, such as age, sex, blood lipids, blood pressure, smoking, diabetes, and body mass index (BMI) as an indicator of overweight and obesity. The National Cholesterol Education Program (NCEP) Adult Treatment Panel III defines elevated plasma levels of low density lipoprotein (LDL) cholesterol (LDL-C≧160 mg/dL), and low levels of high density lipoprotein (HDL) cholesterol (HDL-C≦40 mg/dL) as independent risk factors for CHD. Many prospective epidemiological studies have indicated that a decreased HDL-C level is a significant independent risk factor for heart disease, while increased HDL-C levels≧60 mg/dL (≧1.55 mmol) have a protective role against CHD.

Nicotinic acid (Niacin), a vitamin of the B complex, is used for almost 40 years as a lipid-lowering drug with a favorable profile for all lipoprotein classes. Numerous clinical studies have shown the beneficial effects of niacin, demonstrating a reduction of coronary artery disease and overall mortality. Niacin is the most potent agent currently available to raise HDL. It has been proposed that niacin's main mode of action is through inhibition of lipolysis in the adipose tissue having as a result the reduction of free fatty acids (FFA) in plasma and liver and consequently the decreased production of very low density lipoproteins (VLDL), accounting for the reduction of total cholesterol (TC), triglycerides (TGs), and LDL-C. Due to the decreased TG rich lipoproteins levels, less modification of HDL particles occurs upon the action of cholesteryl ester transfer protein (CETP), resulting in a decreased catabolism of HDL. A direct inhibition of lipoprotein AI-HDL (LPAI-HDL) particle uptake by the liver has been also proposed, accounting for the overall HDL raising properties of niacin (Jin et al Arterioscler. Thromb. Vasc. Biol. 1997, 17, 2020-2028).

Niacin also has anti-diabetic, anti-thrombotic and anti-inflammatory properties that contribute to the overall cardioprotective effects. Through a variety of mechanisms niacin reduces thrombosis, such as the reduction of lipoprotein (a) (Lp(a)) which is a potent inhibitor of fibrinolytic activity, and it is the only currently approved drug that effectively reduces the serum levels of Lp(a) (Carlson et al. J. Intern. Med. 1989, 226, 271-6). Inflammation is a critical component of atherosclerosis, leading to recruitment of macrophages which both promote plaque development and decrease plaque stability thus increasing cardiovascular risk. Niacin has been suggested to have anti-inflammatory properties, such as the reduction of C-reactive protein (CRP) levels (Grundy et al. Arch. Intern. Med. 2002, 162, 1568-76). Several prospective studies have established a strong and direct correlation between cardiovascular risk and CRP levels, a measure of vascular inflammation. Extensive use of niacin has been hampered due to side effects, mainly intense cutaneous flushing.

Recently HM74A/HM74, a G-protein coupled receptor (GPCR), was identified as a receptor for niacin and proposed as the mediator of the niacin effects (Wise et al. J. Biol. Chem. 2003, 278 (11) 9869-9874 and Soga et al Biochem Biophys Res Commun 2003 303 (1) 364-369). In support, deletion of the PUMA-G (HM74A orthologue) in mice abrogated the niacin effects on reduction of plasma free fatty acids and triglycerides (Tunaru et al Nature Medicine 2003, (3) 352-255).

SUMMARY OF THE INVENTION

In one embodiment of the present invention, provided is a compound of formula (I):

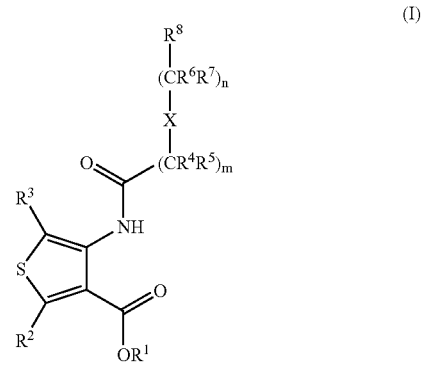

wherein
X is O, S, SO$_2$, NR$^9$, —C(O)NR$^9$—, —NR$^9$C(O)—, —CH$_2$—, —C═C— or —C≡C—;
R$^1$ is hydrogen or lower-alkyl;
R$^2$ is hydrogen, halogen, lower-alkyl or fluoro-lower-alkyl;

$R^3$ is hydrogen, halogen, lower-alkyl or fluoro-lower-alkyl;

$R^4$, $R^5$, $R^6$ and $R^7$ independently from each other are hydrogen, halogen, lower-alkyl, lower-alkoxy, fluoro-lower-alkyl or fluoro-lower-alkoxy, or $R^4$ and $R^5$ are bound together to form a cycloalkyl together with the carbon atom to which they are attached and —$R^4$—$R^5$— is —(CH$_2$)$_{2-6}$—, or $R^6$ and $R^7$ are bound together to form a cycloalkyl together with the carbon atom to which they are attached and —$R^6$—$R^7$— is —(CH$_2$)$_{2-6}$—;

or;

$R^4$ and $R^6$ are bound together to form a ring and —$R^4$—$R^6$— is —(CH$_2$)$_{2-6}$—;

$R^8$ is aryl or heteroaryl, which aryl or heteroaryl is optionally substituted with 1 to 3 substituents selected from the group consisting of halogen, lower-alkyl, hydroxy-lower-alkyl, lower-alkoxy, fluoro-lower-alkoxy, carboxy, carboxy-lower-alkyl, lower-alkoxy-carbonyl, lower-alkoxy-carbonyl-lower-alkyl, $R^{10}R^{11}NC(O)$, $R^{10}R^{11}NC(O)$-lower-alkyl, fluoro-lower-alkyl, $R^{10}R^{11}N$-lower-alkyl, lower-alkyl-SO$_2$, lower-alkyl-SO$_2$O, lower-alkyl-SO$_2$—NR$^{10}$, $R^{10}R^{11}NSO_2$, cyano, NO$_2$, cycloalkyl, lower-alkoxy-lower-alkyl, lower-alkenyl, lower-alkinyl, fluoro-lower-alkoxy-lower-alkyl, cyano-lower-alkyl, phenyl and heteroaryl, which phenyl or heteroaryl is optionally substituted with 1 to 3 substituents selected from the group consisting of halogen, lower-alkyl, lower-alkoxy, lower-alkyl-C(O) and lower-alkyl-C(O)N($R^{10}$);

$R^9$ is hydrogen, lower-alkyl or fluoro-lower-alkyl;

$R^{10}$ and $R^{11}$ independently from each other are hydrogen or lower-alkyl;

m is 0, 1, 2 or 3;

n is 0, 1, 2 or 3;

and pharmaceutically acceptable salts and pharmaceutically acceptable esters thereof, with the proviso that the compound of formula (I) is not 2-methyl-4-[[(phenylmethoxy)carbonyl]amino]-3-thiophenecarboxylic acid methyl ester.

In another embodiment of the present invention, provided is a process for the manufacture of a compound of formula (I), comprising the steps of: reacting a compound of formula (II)

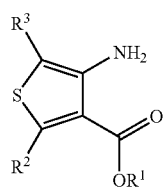

(II)

with a compound of formula (III),

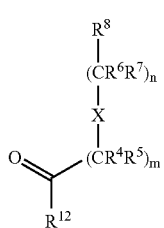

(III)

wherein $R^1$, $R^2$, $R^3$, $R^4$, $R^5$, $R^6$, $R^7$, $R^8$, X, m and n are as defined above and $R^{12}$ is OH, Cl, Br, or a carboxylic acid moiety to form an anhydride;

or hydrolysis of a compound of formula (Ia)

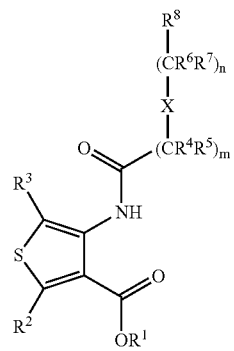

(Ia)

wherein $R^2$, $R^3$, $R^4$, $R^5$, $R^6$, $R^7$, $R^8$, X, m and n are as defined above and $R^1$ is lower-alkyl.

In a further embodiment of the present invention, provided is a pharmaceutical composition, comprising a therapeutically effective amount of a compound according to formula I or 2-methyl-4-[[(phenylmethoxy)carbonyl]amino]-3-thiophenecarboxylic acid methyl ester, and a pharmaceutically acceptable carrier and/or adjuvant.

In a yet another embodiment of the present invention, provided is a method for the treatment and/or prevention of diseases which are modulated by HM74A agonists, comprising the step of administering a therapeuctically effective amount of a compound according to formula I or 2-methyl-4-[[(phenylmethoxy)carbonyl]amino]-3-thiophenecarboxylic acid methyl ester to a human being or animal in need thereof.

DETAILED DESCRIPTION

The novel compounds of the present invention exceed the compounds known in the art, inasmuch as they bind to and activate HM74A. The compounds of the present invention are selective for HM74A by which is meant that they show greater affinity for HM74A than for HM74. The compounds of the present invention are expected to have an enhanced therapeutic potential and exhibit reduced side effects compared to nicotinic acid. The compounds of the present invention can be used as medicaments for the treatment and/or prevention of diseases which are modulated by HM74A agonists. Examples of such diseases are increased lipid and cholesterol levels, particularly dyslipidemia, low HDL-cholesterol, atherosclerotic diseases, hypertriglyceridemia, thrombosis, angina pectoris, peripheral vascular disease, stroke, diabetes, particularly non-insulin dependent diabetes mellitus, metabolic syndrome, Alzheimer's disease, Parkinson's disease, schizophrenia, sepsis, inflammatory diseases (such as e.g. asthma, colitis, pancreatitis, cholestasis/fibrosis of the liver, and diseases that have an inflammatory component such as e.g. Alzheimer's disease or impaired/improvable cognitive function).

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Alkyl groups can be substituted as described below for lower-alkyl. Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. Lower-alkyl groups can optionally be substituted, e.g. by hydroxy or cyano. Such substituted lower-alkyl-groups are referred to as "hydroxy-lower-alkyl" or "cyano-lower-alkyl" respectively.

The term "fluoro-lower-alkyl" refers to lower-alkyl groups which are mono- or multiply substituted with fluorine. Examples of fluoro-lower-alkyl groups are e.g. $CFH_2$, $CF_2H$, $CF_3$, $CF_3CH_2$, $CF_3(CH_2)_2$, $(CF_3)_2CH$ and $CF_2H—CF_2$.

The term "alkenyl", alone or in combination with other groups, stands for a straight-chain or branched hydrocarbon residue comprising an olefinic bond and up to 20, preferably up to 16 carbon atoms. The term "lower-alkenyl" refers to a straight-chain or branched hydrocarbon residue comprising an olefinic bond and up to 7, preferably up to 4 carbon atoms, such as e.g. 2-propenyl.

The term "alkinyl", alone or in combination with other groups, stands for a straight-chain or branched hydrocarbon residue comprising a triple bond and up to 20, preferably up to 16 carbon atoms. The term "lower-alkinyl" refers to a straight-chain or branched hydrocarbon residue comprising a triple bond and up to 7, preferably up to 4 carbon atoms, such as e.g. 2-propinyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —$NH_2$, methylamino, ethylamino, dimethylamino, diethylamino, methyl-ethylamino, pyrrolidin-1-yl or piperidino etc., preferably primary amino, dimethylamino and diethylamino and particularly dimethylamino.

The term "cycloalkyl" refers to a monovalent carbocyclic radical of 3 to 10 carbon atoms, preferably 3 to 7 carbon atoms, more preferably 3 to 6 carbon atoms, such as cyclopropyl, cyclobutyl, cyclopentyl, or cyclohexyl.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl. Examples of fluoro-lower-alkoxy groups are e.g. $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O.

The term "aryl", alone or in combination, relates to the phenyl or naphthyl group, preferably the phenyl group, which can optionally be substituted by 1 to 5, preferably 1 to 3 substituents independently selected from the group consisting of halogen, lower-alkyl, hydroxy-lower-alkyl, lower-alkoxy, fluoro-lower-alkoxy, carboxy, carboxy-lower-alkyl, lower-alkoxy-carbonyl, lower-alkoxy-carbonyl-lower-alkyl, $H_2NC(O)$, (H,lower-alkyl)NC(O), (lower-alkyl)$_2$NC(O), $H_2NC(O)$-lower-alkyl, (H,lower-alkyl)NC(O)-lower-alkyl, (lower-alkyl)$_2$NC(O)-lower-alkyl, fluoro-lower-alkyl, $H_2N$-lower-alkyl, (H,lower-alkyl)N-lower-alkyl, (lower-alkyl)$_2$N-lower-alkyl, lower-alkyl-$SO_2$, lower-alkyl-$SO_2$O, lower-alkyl-$SO_2$—NH, lower-alkyl-$SO_2$—N(lower-alkyl), $H_2NSO_2$, (H,lower-alkyl)N$SO_2$, (lower-alkyl)$_2$N$SO_2$, cyano, cycloalkyl, lower-alkoxy-lower-alkyl, lower-alkenyl, lower-alkinyl, fluoro-lower-alkoxy-lower-alkyl, cyano-lower-alkyl, optionally substituted phenyl and optionally substituted heteroaryl. Other possible substituents are e.g. hydroxy, amino, $NO_2$, dioxo-lower-alkylene (forming e.g. a benzodioxyl group), lower-alkylcarbonyl, lower-alkylcarbonyloxy, lower-alkylcarbonyl-NH, cycloalkyl, phenyl and phenyloxy. Preferred substituents are halogen, lower-alkyl, cycloalkyl and optionally substituted phenyl. Furthermore, aryl groups can preferably be substituted as described in the description and claims below.

The term "heteroaryl" refers to an aromatic 5 to 6 membered monocyclic ring or 9 to 10 membered bicyclic ring which can comprise 1, 2 or 3 atoms selected from nitrogen, oxygen and/or sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzoimidazolyl, indolyl, indazolyl, benzoisothiazolyl, benzoxazolyl, benzoisoxazolyl and quinolinyl. A preferred heteroaryl group is pyridinyl. Other preferred heteroaryl groups are pyrimidinyl and pyrazinyl. A heteroaryl group may optionally have a substitution pattern as described earlier in connection with the term "aryl". Furthermore, heteroaryl groups can preferably be substituted as described in the description and claims below.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

Compounds of formula (I) in which a COOH group is present can form salts with bases. Examples of such salts are alkaline, earth-alkaline and ammonium salts such as e.g. Na—, K—, Ca—, Mg— and trimethylammonium-salt. The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes pharmaceutically acceptable solvates.

In detail, the present invention relates to compounds of formula (I)

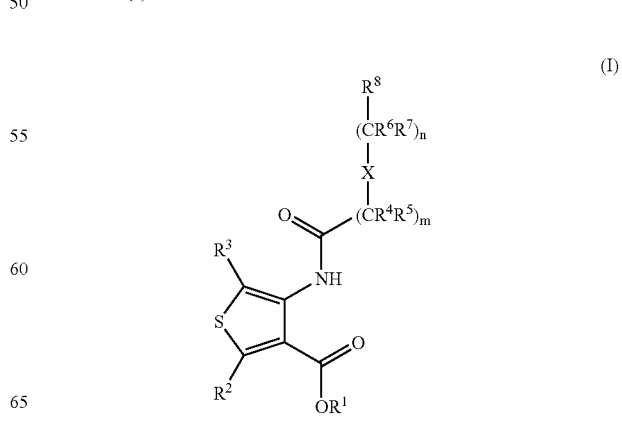

wherein

X is O, S, SO$_2$, NR$^9$, —C(O)NR$^9$—, —NR$^9$C(O)—, —CH$_2$—, —C=C— or —C≡C—;

R$^1$ is hydrogen or lower-alkyl;

R$^2$ is hydrogen, halogen, lower-alkyl or fluoro-lower-alkyl;

R$^3$ is hydrogen, halogen, lower-alkyl or fluoro-lower-alkyl;

R$^4$, R$^5$, R$^6$ and R$^7$ independently from each other are hydrogen, halogen, lower-alkyl, lower-alkoxy, fluoro-lower-alkyl or fluoro-lower-alkoxy, or R$^4$ and R$^5$ are bound together to form a cycloalkyl together with the carbon atom to which they are attached and —R$^4$—R$^5$— is —(CH$_2$)$_{2-6}$—, or R$^6$ and R$^7$ are bound together to form a cycloalkyl together with the carbon atom to which they are attached and —R$^6$—R$^7$— is —(CH$_2$)$_{2-6}$—;

or;

R$^4$ and R$^6$ are bound together to form a ring and —R$^4$—R$^6$— is —(CH$_2$)$_{2-6}$—;

R$^8$ is aryl or heteroaryl, which aryl or heteroaryl is optionally substituted with 1 to 3 substituents selected from the group consisting of halogen, lower-alkyl, hydroxy-lower-alkyl, lower-alkoxy, fluoro-lower-alkoxy, carboxy, carboxy-lower-alkyl, lower-alkoxy-carbonyl, lower-alkoxy-carbonyl-lower-alkyl, R$^{10}$R$^{11}$NC(O), R$^{10}$R$^{11}$NC(O)-lower-alkyl, fluoro-lower-alkyl, R$^{10}$R$^{11}$N-lower-alkyl, lower-alkyl-SO$_2$, lower-alkyl-SO$_2$O, lower-alkyl-SO$_2$—NR$^{10}$, R$^{10}$R$^{11}$NSO$_2$, cyano, NO$_2$, cycloalkyl, lower-alkoxy-lower-alkyl, lower-alkenyl, lower-alkinyl, fluoro-lower-alkoxy-lower-alkyl, cyano-lower-alkyl, phenyl and heteroaryl, which phenyl or heteroaryl is optionally substituted with 1 to 3 substituents selected from the group consisting of halogen, lower-alkyl, lower-alkoxy, lower-alkyl-C(O) and lower-alkyl-C(O)N(R$^{10}$);

R$^9$ is hydrogen, lower-alkyl or fluoro-lower-alkyl;

R$^{10}$ and R$^{11}$ independently from each other are hydrogen or lower-alkyl;

m is 0, 1, 2 or 3;

n is 0, 1, 2 or 3;

and pharmaceutically acceptable salts and pharmaceutically acceptable esters thereof, with the proviso that the compound of formula (I) is not 2-methyl-4-[[(phenylmethoxy)carbonyl]amino]-3-thiophenecarboxylic acid methyl ester.

Compounds of formula (I) are individually preferred and physiologically acceptable salts thereof are individually preferred and pharmaceutically acceptable esters thereof are individually preferred, with the compounds of formula (I) being particularly preferred.

The compounds of formula (I) can have one or more asymmetric C atoms and can therefore exist as an enantiomeric mixture, diastereomeric mixture or as optically pure compounds.

Preferred compounds of formula (I) as described above are those, wherein R$^4$, R$^5$, R$^6$ and R$^7$ independently from each other are hydrogen, lower-alkyl, lower-alkoxy, fluoro-lower-alkyl or fluoro-lower-alkoxy, or R$^4$ and R$^5$ are bound together to form a cycloalkyl together with the carbon atom to which they are attached and —R$^4$—R$^5$— is —(CH$_2$)$_{2-6}$—, or R$^6$ and R$^7$ are bound together to form a cycloalkyl together with the carbon atom to which they are attached and —R$^6$—R$^7$— is —(CH$_2$)$_{2-6}$—; and R$^8$ is aryl or heteroaryl, which aryl or heteroaryl is optionally substituted with 1 to 3 substituents selected from the group consisting of halogen, lower-alkyl, hydroxy-lower-alkyl, lower-alkoxy, fluoro-lower-alkoxy, carboxy, carboxy-lower-alkyl, lower-alkoxy-carbonyl, lower-alkoxy-carbonyl-lower-alkyl, R$^{10}$R$^{11}$NC(O), R$^{10}$R$^{11}$NC(O)-lower-alkyl, fluoro-lower-alkyl, R$^{10}$R$^{11}$N-lower-alkyl, lower-alkyl-SO$_2$, lower-alkyl-SO$_2$O, lower-alkyl-SO$_2$—NR$^{10}$, R$^{10}$R$^{11}$NSO$_2$, cyano, cycloalkyl, lower-alkoxy-lower-alkyl, lower-alkenyl, lower-alkinyl, fluoro-lower-alkoxy-lower-alkyl, cyano-lower-alkyl, phenyl and heteroaryl, which phenyl or heteroaryl is optionally substituted with 1 to 3 substituents selected from the group consisting of halogen, lower-alkyl, lower-alkoxy, lower-alkyl-C(O) and lower-alkyl-C(O)N(R$^{10}$), wherein R$^{10}$ and R$^{11}$ are as defined above.

In a preferred embodiment, X is O, —CH$_2$— or NR$^9$ and R$^9$ is as above. Preferred compounds of formula (I) as defined above are those, wherein X is O or —CH$_2$—, preferably those, wherein X is O.

Furthermore, those compounds are preferred, wherein R$^1$ is hydrogen. Other preferred compounds are those, wherein R$^2$ is hydrogen. Other preferred compounds are those, wherein R$^3$ is hydrogen or lower-alkyl, preferably wherein R$^3$ is hydrogen.

Another preferred embodiment of the present invention relates to compounds of formula (I) as described above, wherein R$^4$, R$^5$, R$^6$ and R$^7$ independently from each other are hydrogen, halogen or lower-alkyl. A preferred embodiment of the present invention relates to compounds of formula (I) as described above, wherein R$^4$, R$^5$, R$^6$ and R$^7$ independently from each other are hydrogen or lower-alkyl, preferably wherein R$^4$, R$^5$, R$^6$ and R$^7$ independently from each other are hydrogen or methyl. In cases, wherein m or n are larger than 1, more than one R$^4$, R$^5$, R$^6$ or R$^7$ occur. In such cases, the individual R$^4$, R$^5$, R$^6$ or R$^7$ can be equal or different. For example, if m is 3 and R$^4$ and R$^5$ are hydrogen or lower-alkyl, the group —(CR$^4$R$^5$)$_3$— can e.g. be —CH(CH$_3$)—CH$_2$—CH$_2$—. Furthermore, in cases wherein m or n are larger than 1, it is preferred that only one R$^4$ and R$^5$ or R$^6$ and R$^7$ are bound together to form a cycloalkyl.

Compounds as defined above, wherein R$^8$ is aryl or heteroaryl, which aryl or heteroaryl is optionally substituted with 1 to 3 substituents selected from the group consisting of halogen, lower-alkyl, lower-alkoxy, fluoro-lower-alkoxy, fluoro-lower-alkyl, cyano, NO$_2$, cycloalkyl, pyrimidinyl, pyrazinyl, pyridinyl and phenyl, which phenyl is optionally substituted with 1 to 3 substituents selected from the group consisting of halogen, lower-alkyl, lower-alkoxy, lower-alkyl-C(O) and lower-alkyl-C(O)N(R$^{10}$), and R$^{10}$ is as defined above, are preferred. In the compounds of the present invention, R$^8$ preferably is aryl or heteroaryl, which aryl or heteroaryl is optionally substituted with 1 to 3 substituents selected from the group consisting of halogen, lower-alkyl, cycloalkyl and phenyl, which phenyl is optionally substituted with 1 to 3 substituents selected from the group consisting of halogen, lower-alkyl, lower-alkoxy, lower-alkyl-C(O) and lower-alkyl-C(O)N(R$^{10}$). More preferably, R$^8$ is phenyl or pyridinyl, which phenyl or pyridinyl is optionally substituted with 1 to 3 substituents selected from the group consisting of halogen, lower-alkyl, cycloalkyl and phenyl, which phenyl is optionally substituted with 1 to 3 substituents selected from the group consisting of halogen and lower-alkoxy. Even more preferably, R$^8$ is 4'-fluoro-biphenyl-4-yl, biphenyl-4-yl, 2'-methoxy-biphenyl-4-yl, 5-(4-fluoro-phenyl)-pyridin-2-yl, 2-chloro-phenyl, phenyl, 3,4-dichloro-phenyl, 4-cyclopentyl-phenyl, 4-tert-butyl-phenyl or 5-(2-fluoro-phenyl)-pyridin-2-yl. Other particularly preferred compounds are those, wherein R$^8$ is 4-pyrimidin-2-yl-phenyl, 4-pyrazin-2-yl-phenyl, 4-pyridin-2-yl-phenyl, 4-pyridin-3-yl-phenyl or biphenyl-3-yl.

Other preferred compounds of the present invention are those, wherein m is 1, 2 or 3, more preferably 1 or 3. Other preferred compounds of the present invention are those, wherein n is 0.

Further preferred compounds of formula (I) as described above are those, wherein $R^9$ is hydrogen. Compounds as described above, wherein $R^{10}$ and $R^{11}$ are hydrogen, are also preferred.

In particular, preferred compounds are the compounds of formula (I) described in the examples as individual compounds as well as pharmaceutically acceptable salts as well as pharmaceutically acceptable esters thereof.

Preferred compounds of formula (I) are those selected from the group consisting of:
4-[2-(4'-Fluoro-biphenyl-4-yloxy)-acetylamino]-thiophene-3-carboxylic acid,
4-[2-(Biphenyl-4-yloxy)-acetylamino]-thiophene-3-carboxylic acid,
4-[2-(2'-Methoxy-biphenyl-4-yloxy)-acetylamino]-thiophene-3-carboxylic acid,
4-[2-(3'-Chloro-biphenyl-4-yloxy)-acetylamino]-thiophene-3-carboxylic acid,
4-[2-(2'-Methyl-biphenyl-4-yloxy)-acetylamino]-thiophene-3-carboxylic acid,
4-[2-(3'-Acetylamino-biphenyl-4-yloxy)-acetylamino]-thiophene-3-carboxylic acid,
4-[2-(3'-Methoxy-biphenyl-4-yloxy)-acetylamino]-thiophene-3-carboxylic acid,
4-[2-(3'-Acetyl-biphenyl-4-yloxy)-acetylamino]-thiophene-3-carboxylic acid,
4-(5-Phenyl-pentanoylamino)-thiophene-3-carboxylic acid,
4-{2-[5-(2-Methoxy-phenyl)-pyridin-2-yloxy]-acetylamino}-thiophene-3-carboxylic acid,
4-{2-[5-(4-Fluoro-phenyl)-pyridin-2-yloxy]-acetylamino}-thiophene-3-carboxylic acid,
4-[4-(2-Chloro-phenoxy)-butyrylamino]-thiophene-3-carboxylic acid,
4-[4-(3-Chloro-phenoxy)-butyrylamino]-thiophene-3-carboxylic acid,
4-[4-(2-Fluoro-phenoxy)-butyrylamino]-thiophene-3-carboxylic acid,
4-[4-(3-Fluoro-phenoxy)-butyrylamino]-thiophene-3-carboxylic acid,
4-(4-Phenoxy-butyrylamino)-thiophene-3-carboxylic acid,
4-(2-Methyl-4-phenoxy-butyrylamino)-thiophene-3-carboxylic acid,
4-[2-(3,4-Dichloro-phenoxy)-acetylamino]-thiophene-3-carboxylic acid,
4-{2-[5-(2-Chloro-phenyl)-pyridin-2-yloxy]-acetylamino}-thiophene-3-carboxylic acid,
4-[2-(4-Cyclohexyl-phenoxy)-acetylamino]-thiophene-3-carboxylic acid,
4-[2-(4-Cyclopentyl-phenoxy)-acetylamino]-thiophene-3-carboxylic acid,
4-[2-(4-Isopropyl-phenoxy)-acetylamino]-thiophene-3-carboxylic acid,
4-[2-(4-tert-Butyl-phenoxy)-acetylamino]-thiophene-3-carboxylic acid,
4-[2-(4-sec-Butyl-phenoxy)-acetylamino]-thiophene-3-carboxylic acid, and
4-{2-[5-(2-Fluoro-phenyl)-pyridin-2-yloxy]-acetylamino}-thiophene-3-carboxylic acid, and pharmaceutically acceptable salts and esters thereof.

Particularly preferred compounds of formula (I) are those selected from the group consisting of
4-[2-(4'-Fluoro-biphenyl-4-yloxy)-acetylamino]-thiophene-3-carboxylic acid;
4-[2-(Biphenyl-4-yloxy)-acetylamino]-thiophene-3-carboxylic acid;
4-[2-(2'-Methoxy-biphenyl-4-yloxy)-acetylamino]-thiophene-3-carboxylic acid;
4-{2-[5-(4-Fluoro-phenyl)-pyridin-2-yloxy]-acetylamino}-thiophene-3-carboxylic acid;
4-[4-(2-Chloro-phenoxy)-butyrylamino]-thiophene-3-carboxylic acid;
4-(2-Methyl-4-phenoxy-butyrylamino)-thiophene-3-carboxylic acid;
4-[2-(3,4-Dichloro-phenoxy)-acetylamino]-thiophene-3-carboxylic acid;
4-[2-(4-Cyclopentyl-phenoxy)-acetylamino]-thiophene-3-carboxylic acid;
4-[2-(4-tert-Butyl-phenoxy)-acetylamino]-thiophene-3-carboxylic acid; and
4-{2-[5-(2-Fluoro-phenyl)-pyridin-2-yloxy]-acetylamino}-thiophene-3-carboxylic acid;

and pharmaceutically acceptable salts and esters thereof.

Other preferred compounds of formula (I) are those selected from the group consisting of:
4-[2-(4-Pyrimidin-2-yl-phenoxy)-acetylamino]-thiophene-3-carboxylic acid,
4-[2-(4-Pyrazin-2-yl-phenoxy)-acetylamino]-thiophene-3-carboxylic acid,
4-[2-(4-Pyridin-2-yl-phenoxy)-acetylamino]-thiophene-3-carboxylic acid,
4-[2-(4-Pyridin-3-yl-phenoxy)-acetylamino]-thiophene-3-carboxylic acid,
4-[2-(4-Pyridin-4-yl-phenoxy)-acetylamino]-thiophene-3-carboxylic acid,
4-[2-(4-Chloro-phenoxy)-acetylamino]-thiophene-3-carboxylic acid,
4-[2-(3,5-Dichloro-phenoxy)-acetylamino]-thiophene-3-carboxylic acid,
4-[2-(3-Chloro-phenoxy)-acetylamino]-thiophene-3-carboxylic acid,
4-(2-m-Tolyloxy-acetylamino)-thiophene-3-carboxylic acid,
4-[2-(3-Ethyl-phenoxy)-acetylamino]-thiophene-3-carboxylic acid,
4-[2-(3-Nitro-phenoxy)-acetylamino]-thiophene-3-carboxylic acid,
4-[2-(3-Ethoxy-phenoxy)-acetylamino]-thiophene-3-carboxylic acid,
4-[2-(3-Ethynyl-phenoxy)-acetylamino]-thiophene-3-carboxylic acid,
4-[2-(Biphenyl-3-yloxy)-acetylamino]-thiophene-3-carboxylic acid,
4-[2-(3-Chloro-4-cyano-phenoxy)-acetylamino]-thiophene-3-carboxylic acid,
4-[2-(3-Trifluoromethyl-phenoxy)-acetylamino]-thiophene-3-carboxylic acid,
4-[2-(3-Chloro-4-methyl-phenoxy)-acetylamino]-thiophene-3-carboxylic acid,
4-[2-(4-Chloro-3-fluoro-phenoxy)-acetylamino]-thiophene-3-carboxylic acid,
4-[2-(4-Chloro-3-trifluoromethyl-phenoxy)-acetylamino]-thiophene-3-carboxylic acid,
4-[2-(2-Fluoro-5-trifluoromethyl-phenoxy)-acetylamino]-thiophene-3-carboxylic acid,
4-[2-(3-Fluoro-5-trifluoromethyl-phenoxy)-acetylamino]-thiophene-3-carboxylic acid,
4-[2-(3,5-Difluoro-phenoxy)-acetylamino]-thiophene-3-carboxylic acid,
4-[2-(4-Trifluoromethoxy-phenoxy)-acetylamino]-thiophene-3-carboxylic acid,
4-[2-(3,5-Bis-trifluoromethyl-phenoxy)-acetylamino]-thiophene-3-carboxylic acid, 4-[2-(3-Chloro-5-fluoro-phenoxy)-acetylamino]-thiophene-3-carboxylic acid,
4-[2-(3,5-Dibromo-phenoxy)-acetylamino]-thiophene-3-carboxylic acid,
4-[2-(3,5-Dichloro-phenylamino)-acetylamino]-thiophene-3-carboxylic acid,
4-[2-(2-tert-Butyl-pyrimidin-5-yloxy)-acetylamino]-thiophene-3-carboxylic acid,
4-[2-(4'-Fluoro-biphenyl-4-yloxy)-acetylamino]-5-methyl-thiophene-3-carboxylic acid,
4-[2-(3,4-Dichloro-phenoxy)-propionylamino]-thiophene-3-carboxylic acid,
4-[2-(4'-Fluoro-biphenyl-4-yloxy)-propionylamino]-thiophene-3-carboxylic acid,
4-[2-(4-tert-Butyl-phenoxy)-propionylamino]-thiophene-3-carboxylic acid,
4-[2-Fluoro-2-(4'-fluoro-biphenyl-4-yloxy)-acetylamino]-thiophene-3-carboxylic acid,
4-[2-(4-tert-Butyl-phenoxy)-2-fluoro-acetylamino]-thiophene-3-carboxylic acid,
4-[2-(3,4-Dichloro-phenoxy)-2-fluoro-acetylamino]-thiophene-3-carboxylic acid, and
4-[2,2-Difluoro-2-(4'-fluoro-biphenyl-4-yloxy)-acetylamino]-thiophene-3-carboxylic acid, and pharmaceutically acceptable salts and esters thereof.

Other particularly preferred compounds of formula (I) are those selected from the group consisting of:
4-[2-(4-Pyrimidin-2-yl-phenoxy)-acetylamino]-thiophene-3-carboxylic acid,
4-[2-(4-Pyrazin-2-yl-phenoxy)-acetylamino]-thiophene-3-carboxylic acid,
4-[2-(4-Pyridin-2-yl-phenoxy)-acetylamino]-thiophene-3-carboxylic acid,
4-[2-(4-Pyridin-4-yl-phenoxy)-acetylamino]-thiophene-3-carboxylic acid,
4-[2-(Biphenyl-3-yloxy)-acetylamino]-thiophene-3-carboxylic acid,
4-[2-(4-tert-Butyl-phenoxy)-2-fluoro-acetylamino]-thiophene-3-carboxylic acid, and
4-[2,2-Difluoro-2-(4'-fluoro-biphenyl-4-yloxy)-acetylamino]-thiophene-3-carboxylic acid and pharmaceutically acceptable salts and esters thereof.

Preferably, if $R^8$ is heteroaryl which is optionally substituted as described above, $R^8$ is not pyridazinyl, which can optionally be substituted as described above. Preferably, $R^8$ is not aryl which is optionally substituted as described above. More preferably, $R^8$ is not phenyl which is substituted with phenyl, which second phenyl may optionally be substituted as described above. More preferably, $R^8$ is not biphenyl.

More preferably, if $R^1$ is hydrogen or methyl, $R^2$ and $R^3$ are hydrogen, m is 1, $R^4$ and $R^5$ are hydrogen, X is O or —$CH_2$—, n is 0, then $R^8$ is not biphenyl or phenyl-pyridazinyl.

Preferably, the compound of formula (I) is not selected from the group consisting of 4-([[(4-biphenylyloxy)acetyl]amino)-3-thiophenecarboxylic acid, methyl-4-([[(4-biphenylyloxy)acetyl]amino)-3-thiophenecarboxylate, 4-([3-(4-biphenylyloxy)propanoyl]amino)-3-thiophenecarboxylic acid, and methyl-4-([3-(4-biphenylyloxy)propanoyl]amino)-3-thiophenecarboxylate. Furthermore, it is preferred that the compound of formula (I) as described above is not selected from the group consisting of 4-([3-(6-phenyl-3-pyridazinyl)propanoyl]amino)-3-thiophenecarboxylic acid and methyl-4-([3-(6-phenyl-3-pyridazinyl)propanoyl]amino)-3-thiophenecarboxylate.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises reacting a compound of formula (II)

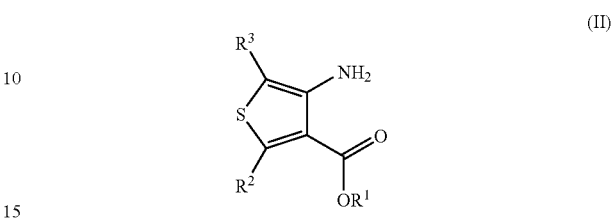

with a compound of formula (III),

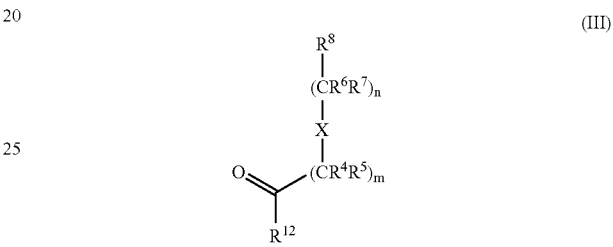

wherein $R^1$, $R^2$, $R^3$, $R^4$, $R^5$, $R^6$, $R^7$, $R^8$, X, m and n are as defined above and $R^{12}$ is OH, Cl, Br, or a carboxylic acid moiety to form an anhydride;

or hydrolysis of a compound of formula (Ia)

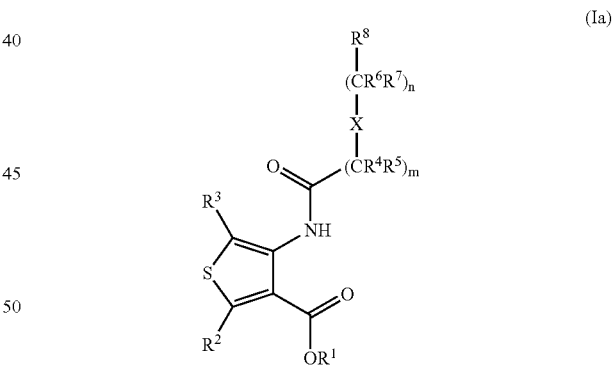

wherein $R^2$, $R^3$, $R^4$, $R^5$, $R^6$, $R^7$, $R^8$, X, m and n are as defined above and $R^1$ is lower-alkyl.

If $R^{12}$ is a carboxylic acid moiety, it is preferably pivaloylic acid, p-nitrobenzoic acid, p-trifluoromethylbenzoic acid, 2,4,6-trichloro benzoic acid, acetic acid, trifluoroacetic acid, carbonic acid monoisobutyl ester, diphenyl phosphinic acid or benzene sulfonic acid to form an asymmetric anhydride, or it is the remainder of a second moiety of formula (III) bound via an oxygen atom to form a symmetric anhydride. Preferably, $R^{12}$ is Cl or Br.

The reaction of a compound of formula (II) with a compound of formula (III) or the reaction of a compound of formula (Ia) can be performed under reaction conditions well known to the person skilled in the art. Such reactions can conveniently be carried out for amide bond formation (process a) with compounds of formula (III) ($R^{12}$=Cl, Br) or with mixed or symmetric anhydrides (III), wherein $R^{12}$ is a carboxylic acid moiety such as e.g. pivaloylic acid, p-nitrobenzoic acid, p-trifluoromethylbenzoic acid, 2,4,6-trichloro benzoic acid, acetic acid, trifluoroacetic acid, carbonic acid monoisobutyl ester, diphenyl phosphinic acid or benzene sulfonic acid or the remainder of a second moiety of formula (III) bound via an oxygen atom to form a symmetric anhydride, in a solvent such as dichloromethane, in the presence of a base such as triethylamine, ethyl-diisopropyl-amine, N-ethylmorpholine or DMAP (dimethyl-pyridin-4-yl-amine) at temperatures between 0° C. and reflux, with compounds of formula (III) ($R^{12}$=OH) in the presence of N-(3-dimethylaminopropyl)-N'-ethyl-carbodiimide-hydrochloride or BOP (benzotriazol-1-yloxytris(dimethylamino)phosphonium hexafluorophoshate) in the presence of a base such as ethyl-diisopropylamine, triethylamine, N-methylmorpholine optionally in the presence of 4-dimethylamino-pyridine, HATU (O-(7-azabenzotriazol-1-yl)-N,N,N',N'-tetramethyluronium hexafluoro-phosphate), TBTU (2-(1H-benzotriazole-1-yl)-1,1,3,3-tetramethyluroniumtetrafluoroborate) or HOBt (1-hydroxybenzo-triazole) in solvents such as dichloromethane, DMF (dimethyl formamide), DMA (dimethylacetamide) or dioxane at temperatures between 0° C. and ambient temperature or for process (b) by treatment with an alkali hydroxide like LiOH or NaOH in a polar solvent such as tetrahydrofuran, methanol, ethanol or water or mixtures thereof. If one of the starting materials of formula (II), (III) or (Ia) contains one or more functional groups which are not stable or are reactive under the reaction conditions, appropriate protecting groups (PG) (as described e.g. in "Protective Groups in Organic Chemistry" by T. W. Greene and P. G. M. Wutts, 2nd Ed., 1991, Wiley N.Y.) can be introduced before the condensation step applying methods well known in the art. Such protecting groups can be removed at a later stage of the synthesis using standard methods described in the literature.

Compounds of the general formula (Ia) can contain one or more stereocenters and can optionally be separated into optically pure enantiomers or diastereomers by methods well known in the art, e.g. by HPLC chromatography, chromatography on a chiral HPLC column, chromatography with a chiral eluant or by derivatization of compound (Ib) ($R^1$=H) with an optically pure alcohol to form esters, which can be separated by conventional HPLC chromatography and then converted back to the enantiomerically pure acids (Ib) ($R^1$=H). In addition, racemic compounds (Ib) can be separated into their antipodes via diastereomeric salts by crystallization with optically pure amines such as e.g. (R) or (S)-1-phenyl-ethylamine, (R) or (S)-1-naphthalen-1-yl-ethylamine, brucine, quinine or quinidine.

The present invention also relates to compounds of formula (I) as defined above, when prepared by a process as described above.

The compounds of formula (I) can be prepared by methods known in the art or as described below in schemes 1 to 4. All starting materials are either commercially available, described in the literature or can be prepared by methods well known in the art. Unless otherwise indicated, $R^1$, $R^2$, $R^3$, $R^4$, $R^5$, $R^6$, $R^7$, $R^8$, $R^9$, $R^{10}$, $R^{11}$, $R^{12}$, X, m and n are as described above.

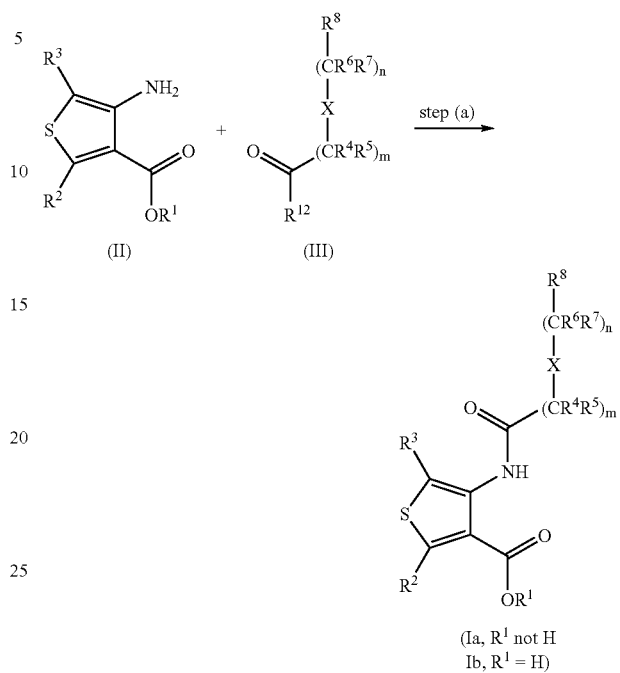

The preparation of compounds of formula (I) is described in scheme 1. The starting materials, amino-thiophens (II) and carboxylic acids (III) ($R^{12}$=OH), carboxylic acid derivatives (III) ($R^{12}$=Cl, Br, etc.) or carboxylic acid anhydrides (III), particularly unsymmetric anhydrides, wherein $R^{12}$ is a deprotonated carboxylic acid moiety such as e.g. pivaloylic acid, p-nitrobenzoic acid, p-trifluoromethylbenzoic acid, 2,4,6-trichloro benzoic acid, acetic acid, trifluoroacetic acid, carbonic acid monoisobutyl ester, diphenyl phosphinic acid or benzene sulfonic acid or the remainder of a second moiety of formula (III) bound via an oxygen atom to form a symmetric anhydride, are either commercially available, described in the literature or can be prepared by methods well known to a person skilled in the art. Reacting compounds of formula (III) with compounds of formula (II) results in the formation of compounds of formula (Ia) or (Ib) (step a). Such amide bond formation reactions are well known in the art. E. g. if $R^{12}$ is equal to chlorine or bromine such an amide bond formation can be performed in a solvent such as dichloromethane, in the presence of a base such as triethylamine, ethyl-diisopropylamine or N-ethylmorpholine at temperatures between 0° C. and ambient temperature. Alternatively, compounds of formula (Ia) or (Ib) may be prepared by treatment of anilines (II) with carboxylic acid anhydrides (III) in a solvent such as dichloromethane, in the presence of a base such as triethylamine, ethyl-diisopropyl-amine or N-ethylmorpholine at temperatures between 0° C. and ambient temperature.

In addition, condensations of amines (II) with carboxylic acids (III) ($R^{12}$=OH) can be performed using well known procedures for amide formation, such as the use of N-(3-dimethylaminopropyl)-N'-ethyl-carbodiimide-hydrochloride, HATU, TBTU or BOP (benzotriazol-1-yloxytris(dimethylamino)phosphonium hexafluorophoshate) in the presence of a base such as ethyl-diisopropyl-amine, triethylamine, N-methylmorpholine optionally in the presence of 4-dimethylamino-pyridine or HOBt (1-hydroxybenzo-triazole) in solvents such as dichloromethane, DMF, DMA or dioxane at temperatures between 0° C. and reflux.

If one of the starting materials (II) or (III) contains one or more functional groups which are not stable or are reactive under the conditions of the amide bond formation, appropriate protecting groups (as described e.g. in "Protective Groups in Organic Chemistry" by T. W. Greene and P. G. M. Wutts, $2^{nd}$ Ed., 1991, Wiley N.Y.) can be introduced before the condensation step applying methods well known in the art. Such protecting groups can be removed at a later stage of the synthesis using standard methods described in the literature.

Compounds of the general formula (Ia) and (Ib) can contain one or more stereocenters and can optionally be separated into optically pure enantiomers or diastereomers by methods well known in the art, e.g. by HPLC chromatography, chromatography on a chiral HPLC column, chromatography with a chiral eluant or by derivatization of compound (Ib) with an optically pure alcohol to form esters, which can be separated by conventional HPLC chromatography and then converted back to the enantiomerically pure acids (Ib) ($R^1$=H). In addition, racemic compounds (Ib) can be separated into their antipodes via diastereomeric salts by crystallization with optically pure amines such as e.g. (R) or (S)-1-phenyl-ethylamine, (R) or (S)-1-naphthalen-1-yl-ethylamine, brucine, quinine or quinidine.

optionally in the presence of anisole in a solvent like dichloromethane or dichloroethane between room temperature and the reflux temperature of the solvents yields carboxylic acids (Ib).

If the ester (Ia) contains one or more functional groups which are not stable under the hydrolysis conditions, appropriate protecting groups (as described e.g. in "Protective Groups in Organic Chemistry" by T. W. Greene and P. G. M. Wutts, $2^{nd}$ Ed., 1991, Wiley N.Y.) can be introduced before the saponification, applying methods well known in the art. Subsequent hydrolysis and removal of the protecting group(s) provides carboxylic acid (Ib).

Compounds of the general formula (Ib) can contain one or more stereocenters and can optionally be separated into optically pure enantiomers or diastereomers by methods well known in the art, e.g. by HPLC chromatography, chromatography on a chiral HPLC column, chromatography with a chiral eluant or by derivatization of compound (Ib) with an optically pure alcohol to form esters, which can be separated by conventional HPLC chromatography and then converted back to the enantiomerically pure acids (Ib). In addition, racemic compounds (Ib) can be separated into their antipodes via diastereomeric salts by crystallization with optically pure amines such as e.g. (R) or (S)-1-phenyl-ethylamine, (R) or (S)-1-naphthalen-1-yl-ethylamine, brucine, quinine or quinidine.

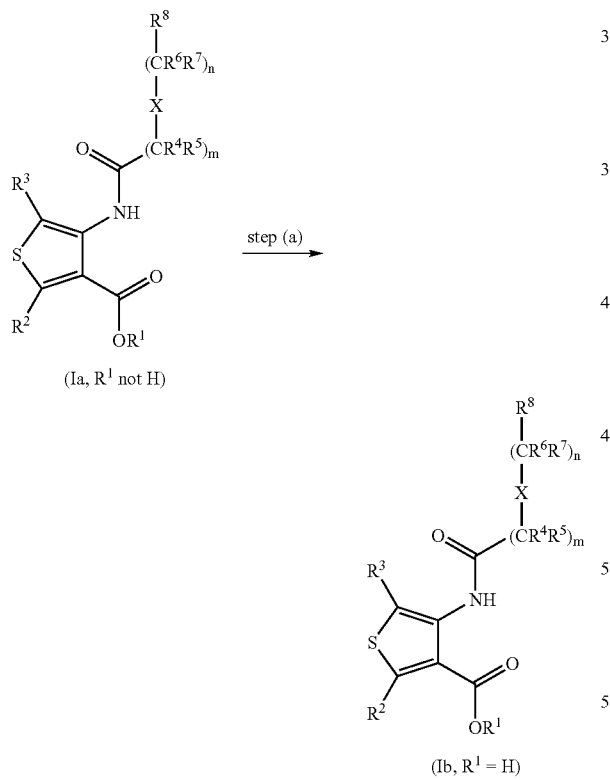

Scheme 2

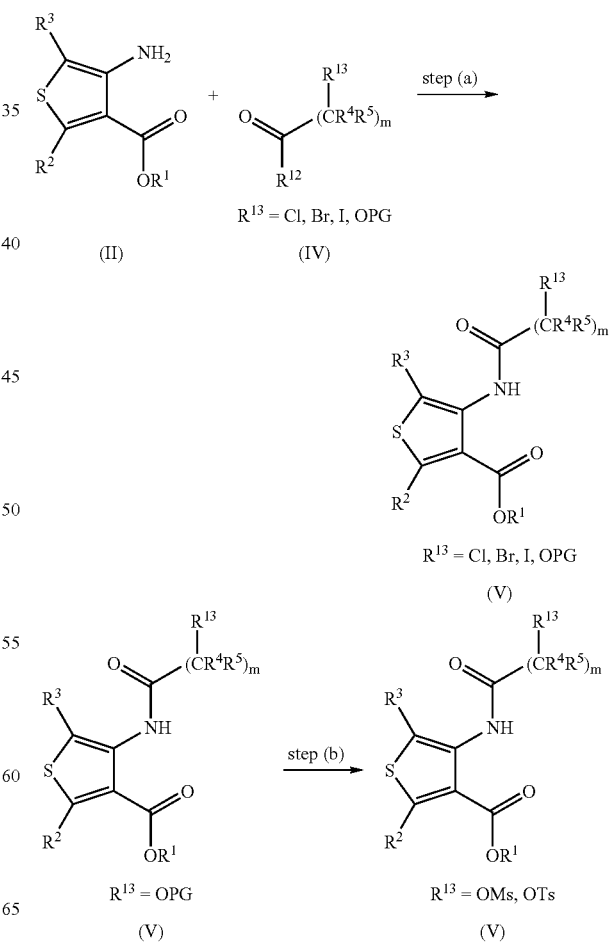

Scheme 3

The preparation of compounds of formula (Ib) with $R^1$=H from compounds of formula (Ia) with $R^1$ not H is described in scheme 2 (step a). These hydrolysis reactions can be performed according to standard procedures, e.g. by treatment with an alkali hydroxide like LiOH or NaOH in a polar solvent such as tetrahydrofuran, methanol, ethanol or water or mixtures thereof to give carboxylic acids (Ib). In case $R^1$ is equal to tert-butyl, treatment with e.g. trifluoroacetic acid,

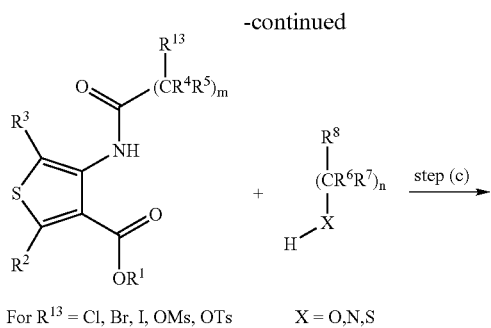

For R$^{13}$ = Cl, Br, I, OMs, OTs    X = O,N,S (V)          (VI)

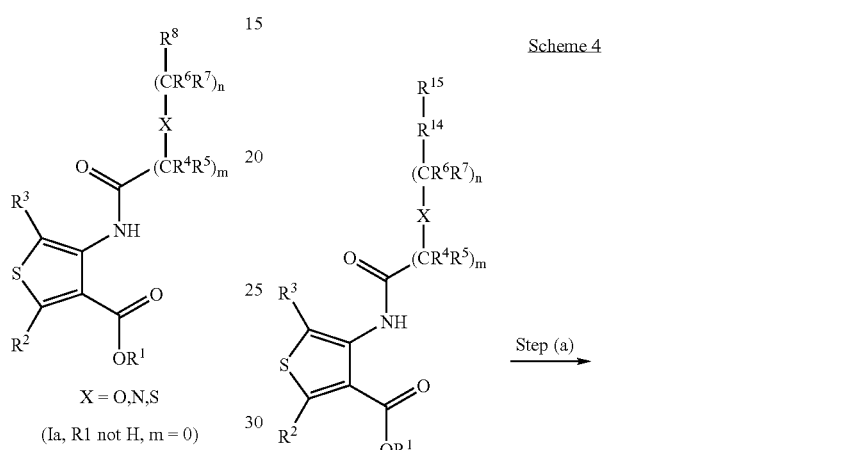

X = O,N,S (Ia, R1 not H, m = 0)

Condensations of amino thiophene (II) with carboxylic acids (IV) (R$^{12}$=OH; R$^3$=Cl, Br, I) or carboxylic acid derivatives (IV) (R$^{12}$=Cl, Br; R$^3$=Cl, Br, I) or carboxylic acid anhydrides (IV) to give amides (V) can be performed using standard procedures described in the literature. E.g. if R$^{12}$ is equal to chlorine, bromine or for the carboxylic acid anhydrides the reaction could be performed in a solvent such as dichloromethane, in the presence of a base such as triethylamine, ethyl-diisopropyl-amine or N-ethylmorpholine at temperatures between 0° C. and ambient temperature (Scheme 3, step a). If R$^{12}$ is equal to OH activating reagents like e.g. N-(3-dimethylaminopropyl)-N'-ethyl-carbodiimide-hydrochloride, HATU, TBTU or BOP (benzotriazol-1-yloxy-tris(dimethylamino)phosphonium hexafluorophoshate) in the presence of a base such as ethyl-diisopropyl-amine, triethylamine, N-methylmorpholine optionally in the presence of 4-dimethylamino-pyridine or HOBt (1-hydroxybenzotriazole) in solvents such as dichloromethane, DMF, DMA or dioxane at temperatures between 0° C. and ambient temperature could be used.

Protected alcohols V (R$^{13}$=OPG) can be deprotected by methods well known to the person skilled in the art (as described e.g. in "Protective Groups in Organic Chemistry" by T. W. Greene and P. G. M. Wutts, 2$^{nd}$ Ed., 1991, Wiley N.Y.). They can then be converted to the corresponding mesylate or tosylate V (R$^{13}$=OMs, OTs) by treatment with methanesulfonyl chloride or para-toluenesulfonyl chloride, respectively, in dichloromethane in the presence of DMAP (dimethylaminopyridine) at temperatures between 0° C. and ambient temperature (scheme 3, step b).

OPG refers to protected alcohols which can be made by methods well known to the person skilled in the art (as described e.g. in "Protective Groups in Organic Chemistry" by T. W. Greene and P. G. M. Wutts, 2$^{nd}$ Ed., 1991, Wiley N.Y.).

Nucleophilic substitution reactions between compounds of formula V and compounds of formula VI to form compounds of formula Ia (Scheme 3, step c) are well know in the art. For example such a reaction can be carried out in a polar solvent such as dimethylformamide in the presence of a base such as potassium carbonate at room temperature or at elevated temperature.

Compounds of formula Ia can be transformed in compounds of formula Ib according to methods described in Scheme 2.

Scheme 4

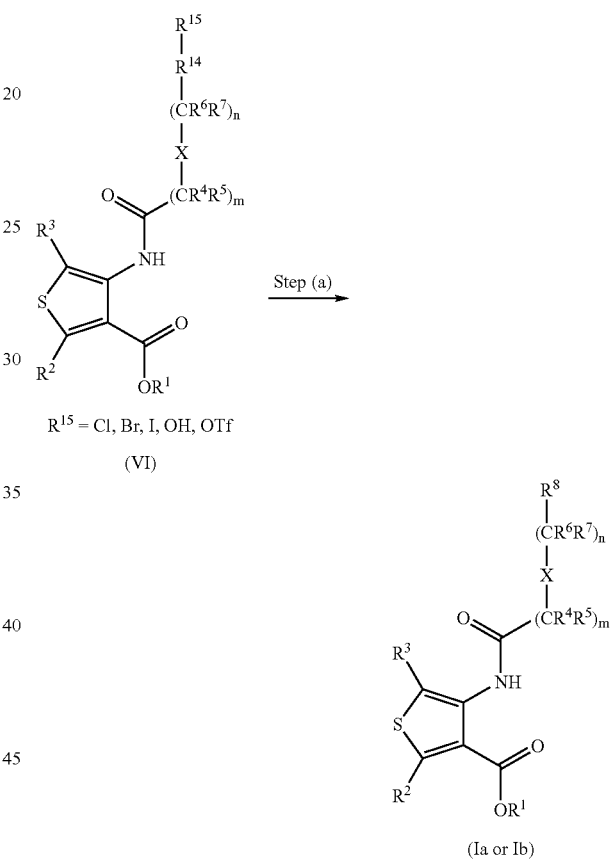

R$^{15}$ = Cl, Br, I, OH, OTf (VI)

(Ia or Ib)

An additional synthetic route towards compounds of formula (Ia or Ib) is depicted in scheme 4, for compounds in which R$^8$ is a substituted aryl or heteroaryl. Starting point are derivatives (VII) in which R$^{14}$ is an aryl or heteroaryl group, in analogy to the definition of R$^8$, which carries a substituent R$^{15}$.

Halides (VII) (R$^{15}$=Cl, Br, I), phenols (VII) (R$^{15}$=OH) or triflates (VII) (R$^{15}$=OTf) can be reacted with alcohols to give ethers (I) using methods well known in the art (scheme 4, step a). Phenols (VII) (R$^{15}$=OH) may be generated from the protected phenols (VII) (R$^{15}$=OPG) prior to use by methods well known to the person skilled in the art (as described e.g. in "Protective Groups in Organic Chemistry" by T. W. Greene and P. G. M. Wutts, 2$^{nd}$ Ed., 1991, Wiley N.Y.) and may be converted to the corresponding triflates (VII) (R$^{15}$=OTf) by standard methods described in the literature, e.g. using PhN(SO$_2$Tf)$_2$ in the presence of a base like cesium carbonate in a solvent like N,N-dimethylformamide at temperatures around ambient temperature or in pyridine with trifluoromethanesulfonic anhydride at 0° C. to ambient temperature. The alcohols are either commercially available, described in the literature or can be prepared by methods well known to a person skilled in the art. If halides (VII) ($R^{15}$=Cl, Br, I) are used as starting material, compounds (I) can e.g. be prepared in the presence of CuI, cesium carbonate and 8-hydroxychinoline in a solvent like 1-methyl-2-pyrrolidone (see for example Z. J. Song et al., Organic Letters, 4, 1623; 2002). Starting from triflates (VII) ($R^{15}$=OTf), ethers (Ia) or (Ib) can be synthesized applying e.g. the procedure from Larock et al. (R. C. Larock et al., Organic Letters, 6, 99; 2004) using CsF in acetonitrile at ambient temperature. In addition, several transition metal mediated procedures for the formation of aryl ethers are reported in the literature (see e.g. J. F. Hartwig et al., J. Am. Chem. Soc., 121, 3224; 1999).

Alternatively, phenols (VI) ($R^{15}$=OH) may be treated with alcohols using Mitsunobu (e.g. O. Mitsunobu, *Synthesis* 1981, 1.) conditions to yield compounds (I). This transformation is preferably carried out with triphenylphosphine and di-tert-butyl-, diisopropyl- or diethyl-azodicarboxylate as reagents, in a solvent like toluene, dichloromethane or tetrahydrofuran at 0° C. to ambient temperature.

Alternatively, compounds (I) may be prepared from phenol (VI) ($R^{15}$=OH) by alkylation with compounds bearing a good leaving group such as Br, Cl, I, MsO, TsO, TfO in solvents such as acetone, acetonitrile, DMF (dimethyl formamide), DMA (dimethacetamide) or THF(tetrahydrofuran) in the presence of bases such as $K_2CO_3$, $Cs_2CO_3$ or ethyl-diiso-propyl-amine at temperatures ranging from ambient temperature to the reflux temperature of the solvent.

Alternatively, compounds (I) may be prepared from aryl halides (VI) ($R^5$=Cl, Br, I) or aryl triflates (VI) ($R^5$=OTf) by Carbon-Carbon bond formation reactions. Such reactions are well known in the art, like e.g. Suzuki, Stille or Heck reactions (Suzuki, A. Acc. *Chem. Res.* 1982, 15, 178; Scott, W. J.; Crisp, G. T.; Stille, J. K. *J. Am. Chem. Soc.* 1984, 106, 4630; Heck, R. F. *Organic React.* 1982, 27, 345 respectively). The counterparts of such reactions are either commercially available, described in the literature or can be prepared by methods well known to a person skilled in the art.

If one of the starting materials (II), (IV), (V), or (VI) contains one or more functional groups which are not stable or are reactive under the conditions of the amide bond formation, appropriate protecting groups (as described e.g. in "Protective Groups in Organic Chemistry" by T. W. Greene and P. G. M. Wutts, $2^{nd}$ Ed., 1991, Wiley N.Y.) can be introduced before the condensation step, applying methods well known in the art. Such protecting groups can be removed at a later stage of the synthesis using standard methods described in the literature.

Compounds of the general formula (I) can contain one or more stereocenters and can optionally be separated into optically pure enantiomers or diastereomers by methods well known in the art, e.g. by HPLC chromatography, chromatography on a chiral HPLC column, chromatography with a chiral eluant or by derivatization with an optically pure alcohol to form esters, which can be separated by conventional HPLC chromatography and then converted back to the enantiomerically pure acids (I). In addition, racemic compounds can be separated into their antipodes via diastereomeric salts by crystallization with optically pure amines such as e.g. (R) or (S)-1-phenyl-ethylamine, (R) or (S)-1-naphthalen-1-yl-ethylamine, brucine, quinine or quinidine.

The conversion of a compound of formula (I) into a pharmaceutically acceptable salt can be carried out by treatment of such a compound with physiologically compatible bases. Examples of such salts are alkaline, earth-alkaline and ammonium salts such as e.g. Na—, K—, Ca— and trimethylammonium-salt. One method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

The conversion of compounds of formula (I) into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluorborate (TBTU). Pharmaceutically acceptable esters can furthermore be prepared by treatment of a suitable hydroxy group present in the molecule with a suitable acid, optionally or if necessary in the presence of a condensating agent as described above.

Insofar as their preparation is not described in the examples, the compounds of formula (I) as well as all intermediate products can be prepared according to analogous methods or according to the methods set forth above. Starting materials are commercially available or known in the art.

As described above, the compounds of formula (I) of the present invention and 2-methyl-4-[[(phenylmethoxy)carbonyl]amino]-3-thiophenecarboxylic acid methyl ester, can be used as medicaments for the treatment and/or prevention of diseases which are modulated by HM74A agonists. Examples of such diseases are increased lipid and cholesterol levels, particularly dyslipidemia, low HDL-cholesterol, atherosclerotic diseases, hypertriglyceridemia, thrombosis, angina pectoris, peripheral vascular disease, stroke, diabetes, particularly non-insulin dependent diabetes mellitus, metabolic syndrome, Alzheimer's disease, Parkinson's disease, schizophrenia, sepsis, inflammatory diseases (such as e.g. asthma, colitis, pancreatitis, cholestasis/fibrosis of the liver, and diseases that have an inflammatory component such as e.g. Alzheimer's disease or impaired/improvable cognitive function). The use as medicament for the treatment of atherosclerosis, low HDL cholesterol levels, non-insulin dependent diabetes mellitus, and the metabolic syndrome is preferred.

The invention therefore also relates to pharmaceutical compositions comprising a compound as described above or 2-methyl-4-[[(phenylmethoxy)carbonyl]amino]-3-thiophenecarboxylic acid methyl ester, and a pharmaceutically acceptable carrier and/or adjuvant.

Further, the invention relates to compounds as described above or 2-methyl-4-[[(phenylmethoxy)carbonyl]amino]-3-thiophenecarboxylic acid methyl ester, for use as therapeutic active substances, especially as therapeutic active substances for the treatment and/or prevention of diseases which are modulated by HM74A agonists, particularly as therapeutically active substances for the treatment and/or prevention of increased lipid levels, increased cholesterol levels, atherosclerotic diseases, dyslipidemia, low HDL-cholesterol, hypertriglyceridemia, thrombosis, angina pectoris, peripheral vascular disease, stroke, diabetes, non-insulin dependent diabetes mellitus, metabolic syndrome, Alzheimer's disease, Parkinson's disease, schizophrenia, impaired or improvable cognitive function, sepsis, inflammatory diseases, asthma, colitis, pancreatitis and cholestasisfibrosis of the liver.

In another embodiment, the invention relates to a method for the treatment and/or prevention of diseases which are modulated by HM74A agonists, particularly for the treatment and/or prevention of increased lipid levels, increased cholesterol levels, atherosclerotic diseases, dyslipidemia, low HDL-cholesterol, hypertriglyceridemia, thrombosis, angina pectoris, peripheral vascular disease, stroke, diabetes, non-insulin dependent diabetes mellitus, metabolic syndrome, Alzheimer's disease, Parkinson's disease, schizophrenia, impaired or improvable cognitive function, sepsis, inflammatory diseases, asthma, colitis, pancreatitis and cholestasisfibrosis of the liver, which method comprises administering a compound as described above or 2-methyl-4-[[(phenylmethoxy)carbonyl]amino]-3-thiophenecarboxylic acid methyl ester, to a human or animal.

The invention further relates to the use of compounds as defined above or 2-methyl-4-[[(phenylmethoxy)carbonyl]amino]-3-thiophenecarboxylic acid methyl ester, for the treatment and/or prevention of diseases which are modulated by HM74A agonists, particularly for the treatment and/or prevention of increased lipid levels, increased cholesterol levels, atherosclerotic diseases, dyslipidemia, low HDL-cholesterol, hypertriglyceridemia, thrombosis, angina pectoris, peripheral vascular disease, stroke, diabetes, non-insulin dependent diabetes mellitus, metabolic syndrome, Alzheimer's disease, Parkinson's disease, schizophrenia, impaired or improvable cognitive function, sepsis, inflammatory diseases, asthma, colitis, pancreatitis and cholestasisfibrosis of the liver.

In addition, the invention relates to the use of compounds as described above or 2-methyl-4-[[(phenylmethoxy)carbonyl]amino]-3-thiophenecarboxylic acid methyl ester, for the preparation of medicaments for the treatment and/or prevention of diseases which are modulated by HM74A agonists, particularly for the treatment and/or prevention of increased lipid levels, increased cholesterol levels, atherosclerotic diseases, dyslipidemia, low HDL-cholesterol, hypertriglyceridemia, thrombosis, angina pectoris, peripheral vascular disease, stroke, diabetes, non-insulin dependent diabetes mellitus, metabolic syndrome, Alzheimer's disease, Parkinson's disease, schizophrenia, impaired or improvable cognitive function, sepsis, inflammatory diseases, asthma, colitis, pancreatitis and cholestasisfibrosis of the liver. Such medicaments comprise a compound as described above.

Prevention and/or treatment of atherosclerosis, low HDL cholesterol levels, non-insulin dependent diabetes mellitus, and the metabolic syndrome is preferred.

In the above mentioned compositions, uses and methods, compounds of formula (I) as described above are preferred over 2-methyl-4-[[(phenylmethoxy)carbonyl]amino]-3-thiophenecarboxylic acid methyl ester.

The following tests were carried out in order to determine the biological activity of the compounds of formula (I).

Primary Radiolabelled Ligand Competition Binding Assay

Nicotinic acid binding assays were performed with membrane preparations. A cell pellet containing $1 \times 10^8$ HEK-293 cells, stably transfected with the HM74A receptor, was resuspended in 3 ml of ice cold Dounce Buffer (10 mM Tris-Cl pH 7.6, 0.5 mM $MgCl_2$) supplemented with Roche protease inhibitor cocktail and homogenized at high speed on a Polytron homogenizer two times for 20 sec on ice. Nuclei and unbroken cells were removed by centrifugation for 5 min at $1,000 \times g$ after the addition of 1 ml of tonicity restoration buffer (10 mM Tris pH 7.6, 0.5 mM $MgCl_2$, 600 mM NaCl). The homogenate was centrifuged at $60,000 \times g$ for 30 min and pellets were resuspended in Tris buffer (50 mM Tris pH 7.4, containing protease inhibitors). Binding reactions contained 20 µg membranes as determined by BCA protein assay (Pierce), 50 nM [$^3$H]-nicotinic acid (Amersham) with or without compound addition in 250 µl of binding buffer (50 mM Tris pH 7.4, 2 mM $MgCl_2$, 0.02% CHAPS). Incubations were carried out at room temperature for 2 hrs and terminated by filtration using a Filtermate Harvester (PerkinElmer) onto GF/C filter plates (Millipore). Bound [$^3$H]-nicotinic acid was determined by scintillation counting using Top Count NXT (PerkinElmer). Compounds were dissolved in a concentration of 10-2 or 10-3 M in DMSO, further dilutions were performed in binding buffer. The effects of compounds were expressed as % inhibition of [$^3$H]-nicotinic acid binding. Sigmoidal curves were fitted using the XLfit3 program (ID Business Solutions Ltd. UK) and $IC_{50}$ values determined.

The compounds of the present invention exhibit $IC_{50}$ values in a range of about 0.001 µM to about 100 µM in the binding assay. Preferably, the compounds of the present invention have $IC_{50}$ values in a range of about 0.001 µM to about 10.0 µM, more preferably about 0.001 µM to about 1 µM.

Secondary Fluorescent Calcium Indicator Assay (FLIPR)

HEK-293 cells were grown in tissue culture medium (DMEM/Nut mix F12 Medium with Glutamax I (Invitrogen), containing 10% FBS) at 37° C. in a 5% $CO_2$ atmosphere. These cells were cultured in 6-well dishes at $3 \times 10^5$ cells/well and double transfected with DNA vectors (pcDNA3.1, Invitrogen) expressing either HM74A or HM74 and the chimeric G protein Gqi9. Two days after transfection the wells were combined and plated in 150 cm² flasks, in the presence of 50 µg/ml Hygromycin (Invitrogen) and 500 µg/ml Geneticin (Gibco). Fourteen days after plating, colonies were picked, expanded and analyzed for expression using a functional assay (FLIPR). Stable transfected HEK-293 cells expressing either HM74A or HM74 and the chimeric G protein Gqi9 were plated at 50,000 cells/well in black 96-well plates with clear bottom (Costar) and cultured to confluency overnight in growth media (DMEM/Nut mix F12 Medium with Glutamax I (Invitrogen), containing 10% FBS) at 37° C. in a humidified cell incubator containing 5% $CO_2$. Growth media was aspirated and replaced with 100 µl of 1×FLIPR Calcium Assay Dye (Molecular Devices) in Hank's balanced salt solution (HBSS) containing 10 mM HEPES, and 250 mM probenecid (Sigma), for 1 hour at 37° C. Cell plates were transferred to a FLIPR unit (Molecular Devices), and 50 µl of 3× compound dilution were added. Fluorescence emissions were measured and the effects of compounds were expressed as % stimulation of maximal nicotinic acid response (100 µM). Sigmoidal curves were fitted using the XLfit3 program (ID Business Solutions Ltd. UK) and $EC_{50}$ values determined.

The compounds of the present invention exhibit $EC_{50}$ values in a range of about 0.001 µM about 100 µM in the FLIPR assay. Preferably, the compounds of the present invention have $EC_{50}$ values in a range of about 0.001 µM to about 10.0 µM; more preferably about 0.001 µM to about 1 µM.

In the following table, $EC_{50}$ values for some of the compounds of the present invention are shown.

| Example | $EC_{50}$ HM74A [µM] |
|---------|----------------------|
| 2       | 0.0487               |
| 11      | 0.131                |
| 23      | 0.225                |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 5000 mg, preferably about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-1000 mg, preferably 1-300 mg, more preferably 1-100 mg, of a compound of formula I.

The following Examples serve to illustrate the present invention in more detail. They are, however, not intended to limit its scope in any manner.

EXAMPLES

General remarks

The reactions were performed under argon where appropriate.

Example 1

4-[2-(4'-Fluoro-biphenyl-4-yloxy)-acetylamino]-thiophene-3-carboxylic acid

Step 1: 4-[2-(4-Iodo-phenoxy)-acetylamino]-thiophene-3-carboxylic acid methyl ester To a solution of 4-(3-chloro-propionylamino)-thiophene-3-carboxylic acid methyl ester ([51486-30-7], 2.0 g, 8.6 mmol) in dimethylformamide (30 mL) was added potassium carbonate (1.77 g, 12.8 mmol) and 4-iodophenol (2.26 g, 10.3 mmol) and the reaction mixture was then stirred overnight at 90° C. To the reaction mixture was added ethyl acetate (approximately 30 mL). The solid was filtered and washed with ethyl acetate. The filtrate was then reduced in vacuo and dissolved in dichloromethane (approximately 50 mL). The solution was filtered again over charcoal and to the filtrate was added isopropylether. After reducing the solution slowly in vacuo the solid was filtered to yield the title compound (3.57 g, 79%).

Mp=135-137° C., MS (m/e): 415.9 (M−H$^-$, 100%).

Step 2: 4-[2-(4'-Fluoro-biphenyl-4-yloxy)-acetylamino]-thiophene-3-carboxylic acid methyl ester To a solution of 4-[2-(4-iodo-phenoxy)-acetylamino]-thiophene-3-carboxylic acid methyl ester (0.1 g, 0.428 mmol) in a mixture of tetrahydrofuran (21 mL) and water (5 mL) was added 4-fluorophenylboronic acid (40.3 mg, 0.288 mmol) and cesium carbonate (313 mg, 0.96 mmol). The solution was then degassed by bubbling a flux of argon for 20 minutes before adding polymer bound tetrakis(triphenylphosphine) palladium (Aldrich-511579, 12.86 mg, 0.009 mmol). The reaction mixture was then stirred for 90 min at 80° C. under argon atmosphere before allowing to cool down to room temperature and diluting with ethyl acetate. The reaction mixture was then filtered; the filtrate was then washed twice with brine and dried over sodium sulfate before being concentrated in vacuo. The residue was then filtered through a pad of silica (SiO$_2$, EtOAc, 100%) to yield the title compound as a light brown solid (138 mg, 99%).

Mp=127-130° C., MS (m/e): 384.1 (M−H$^-$, 100%).

Step 3: 4-[2-(4'-Fluoro-biphenyl-4-yloxy)-acetylamino]-thiophene-3-carboxylic acid To 4-[2-(4'-fluoro-biphenyl-4-yloxy)-acetylamino]-thiophene-3-carboxylic acid methyl ester (100 mg, 0.259 mmol) in ethanol (6 mL) was added a solution of sodium hydroxide (1N, 0.39 mL, 0.39 mmol) and the reaction was stirred at room temperature for 2 days. After such time the reaction mixture was filtered through glass wool and the filtrate was then neutralized by addition of a solution of hydrochloric acid (1N, 0.39 mL). Additional water was added to the solution (in excess of 10 mL) before the precipitate was filtered, washed with water and dried in vacuo to yield the title compound as a white solid (93 mg, 80%).

Mp=244-251° C., MS (m/e): 370.1 (M−H$^-$, 100%).

Example 2

4-[2-(Biphenyl-4-yloxy)-acetylamino]-thiophene-3-carboxylic acid

Step 1: 4-[2-(Biphenyl-4-yloxy)-acetylamino]-thiophene-3-carboxylic acid methyl ester To a solution of 4-(3-chloro-propionylamino)-thiophene-3-carboxylic acid methyl ester ([51486-30-7], 0.1 g, 0.43 mmol) in dimethylformamide (1.5 mL) was added potassium carbonate (0.88 g, 0.64 mmol) and 4-hydroxybiphenyl (0.087 g, 0.514 mmol) and the reaction mixture was then stirred overnight at 90° C. After such time the reaction mixture was allowed to cool to room temperature, water was added (in excess of 5 mL) leading to precipitation. The precipitate was then filtered, washed with water and dried in vacuo to yield the title compound as a white solid (0.16 g, 87%).

Mp=132-135° C., MS (m/e): 368.1 (M+H$^+$, 100%).

Step 2: 4-[2-(Biphenyl-4-yloxy)-acetylamino]-thiophene-3-carboxylic acid

To 4-[2-(biphenyl-4-yloxy)-acetylamino]-thiophene-3-carboxylic acid methyl ester (100 mg, 0.259 mmol) in ethanol (6 mL) was added a solution of sodium hydroxide (1N, 0.41 mL, 0.41 mmol) and the reaction was stirred at room temperature for 30 hours. After such time the reaction mixture was filtered through glass wool and the filtrate was then neutralized by addition of a solution of hydrochloric acid (1N, 0.39 mL). The precipitate was filtered, washed with water and dried in vacuo to yield the title compound as a white solid (96 mg, 80%).

Mp=247-251° C., MS (m/e): 352.2 (M−H$^-$, 100%).

Example 3

4-[2-(2'-Methoxy-biphenyl-4-yloxy)-acetylamino]-thiophene-3-carboxylic acid

In analogy to Example 1 (step 2), from 4-[2-(4-iodo-phenoxy)-acetylamino]-thiophene-3-carboxylic acid methyl ester (example 1, step 1) and 2-methoxybenzeneboronic acid was prepared 4-[2-(2'-methoxy-biphenyl-4-yloxy)-acetylamino]-thiophene-3-carboxylic acid methyl ester.

Mp=148-152° C., MS (m/e): 398.2 (M+H$^+$, 100%).

In analogy to Example 1 (step 3), from 4-[2-(2'-methoxy-biphenyl-4-yloxy)-acetylamino]-thiophene-3-carboxylic acid methyl ester was prepared 4-[2-(2'-methoxy-biphenyl-4-yloxy)-acetylamino]-thiophene-3-carboxylic acid.

Mp=196-199° C., MS (m/e): 382.3 (M−H$^-$, 100%).

Example 4

4-[2-(3'-Chloro-biphenyl-4-yloxy)-acetylamino]-thiophene-3-carboxylic acid

In analogy to Example 1 (step 2 and 3), from 4-[2-(4-iodo-phenoxy)-acetylamino]-thiophene-3-carboxylic acid methyl ester (example 1, step 1) and 3-chlorophenylboronic acid was prepared 4-[2-(3'-chloro-biphenyl-4-yloxy)-acetylamino]-thiophene-3-carboxylic acid.

Mp=216-218° C., MS (m/e): 385.8 (M−H$^-$, 100%).

Example 5

4-[2-(2'-Methyl-biphenyl-4-yloxy)-acetylamino]-thiophene-3-carboxylic acid

In analogy to Example 1 (step 2), from 4-[2-(4-iodo-phenoxy)-acetylamino]-thiophene-3-carboxylic acid methyl ester (example 1, step 1) and o-tolylboronic acid was prepared 4-[2-(2'-methyl-biphenyl-4-yloxy)-acetylamino]-thiophene-3-carboxylic acid methyl ester.

MS (m/e): 382.1 (M+H$^+$, 100%).

In analogy to Example 1 (step 3), from 4-[2-(2'-methyl-biphenyl-4-yloxy)-acetylamino]-thiophene-3-carboxylic acid methyl ester was prepared 4-[2-(2'-methyl-biphenyl-4-yloxy)-acetylamino]-thiophene-3-carboxylic acid.

Mp=207-209° C., MS (m/e): 366.0 (M−H$^-$, 100%).

Example 6

4-[2-(3'-Acetylamino-biphenyl-4-yloxy)-acetylamino]-thiophene-3-carboxylic acid

In analogy to Example 1 (step 2), from 4-[2-(4-iodo-phenoxy)-acetylamino]-thiophene-3-carboxylic acid methyl ester (example 1, step 1) and 3-acetamidobenzeneboronic acid was prepared 4-[2-(3'-acetylamino-biphenyl-4-yloxy)-acetylamino]-thiophene-3-carboxylic acid methyl ester.

MS (m/e): 425.1 (M+H$^+$, 100%).

In analogy to Example 1 (step 3), from 4-[2-(3'-acetylamino-biphenyl-4-yloxy)-acetylamino]-thiophene-3-carboxylic acid methyl ester was prepared 4-[2-(3'-acetylamino-biphenyl-4-yloxy)-acetylamino]-thiophene-3-carboxylic acid.

Mp=250-253° C., MS (m/e): 409.0 (M−H$^-$, 100%).

Example 7

4-[2-(3'-Methoxy-biphenyl-4-yloxy)-acetylamino]-thiophene-3-carboxylic acid

In analogy to Example 1 (step 2) from 4-[2-(4-iodo-phenoxy)-acetylamino]-thiophene-3-carboxylic acid methyl ester (example 1, step 1) and 3-methoxyphenyl boronic acid was prepared 4-[2-(4-iodo-phenoxy)-acetylamino]-thiophene-3-carboxylic acid methyl ester.

MS (m/e): 398.2 (M+H$^+$, 100%).

In analogy to Example 1 (step 3), from 4-[2-(4-iodo-phenoxy)-acetylamino]-thiophene-3-carboxylic acid methyl ester was prepared 4-[2-(3'-methoxy-biphenyl-4-yloxy)-acetylamino]-thiophene-3-carboxylic acid.

Mp=187-189° C., MS (m/e): 382.0 (M−H$^-$, 100%).

Example 8

4-[2-(3'-Acetyl-biphenyl-4-yloxy)-acetylamino]-thiophene-3-carboxylic acid

In analogy to Example 1 (step 2) from 4-[2-(4-iodo-phenoxy)-acetylamino]-thiophene-3-carboxylic acid methyl ester (example 1, step 1) and 3-acetylbenzeneboronic acid was prepared 4-[2-(3'-acetyl-biphenyl-4-yloxy)-acetylamino]-thiophene-3-carboxylic acid methyl ester.

MS (m/e): 410.1 (M+H$^+$, 100%).

In analogy to Example 1 (step 3), from 4-[2-(3'-acetyl-biphenyl-4-yloxy)-acetylamino]-thiophene-3-carboxylic acid methyl ester was prepared 4-[2-(3'-acetyl-biphenyl-4-yloxy)-acetylamino]-thiophene-3-carboxylic acid.

Mp=212-214° C., MS (m/e): 394.1 (M−H$^-$, 100%).

Example 9

4-(5-Phenyl-pentanoylamino)-thiophene-3-carboxylic acid

Step 1:
4-(5-Phenyl-pentanoylamino)-thiophene-3-carboxylic acid methyl ester

To a suspension of methyl 4-aminothiophene-3-carboxylate hydrochloride (100 mg, 0.64 mmol) and triethylamine (200 μl, 1.46 mmol) in dichloromethane (1 mL) was slowly added a solution of benzenepentanoyl chloride (158 mg, 0.83 mmol; [20371-41-9]) in dichloromethane (0.5 ml) at 0° C. The reaction mixture was allowed to warm up to room temperature and stirred for 72 h. The suspension was diluted with dichloromethane, washed with water and brine. The aqueous phase was extracted with dichloromethane. The combined organic layers were dried over sodium sulfate and concentrated in vacuo. The residue was purified by column chromatography (heptane-ethyl acetate: 0-40%) to yield 4-(5-phenyl-pentanoylamino)-thiophene-3-carboxylic acid methyl ester (113 mg, 0.36 mmol, 58%) as colorless oil.

MS (m/e): 318.1 (M+H$^+$, 100%).

Step 2:
4-(5-Phenyl-pentanoylamino)-thiophene-3-carboxylic acid

To a solution of 4-(5-phenyl-pentanoylamino)-thiophene-3-carboxylic acid methyl ester (50 mg, 0.16 mmol) in tetrahydrofuran/methanol 2/1 (1.5 ml) was added a 1 N aqueous LiOH solution (0.95 ml, 0.95 mmol). The reaction mixture was stirred at room temperature for 2 h, acidified with 1 N HCl and extracted two times with ethyl acetate. The combined organic layers were washed with water and brine and dried over sodium sulfate. The solvent was removed under reduced pressure and the crude product was purified by thin layer chromatography (SiO$_2$, dichloromethane) to give the title compound as colorless oil (20 mg, 0.07 mmol, 42%).

MS (m/e): 304.1 (M+H$^+$, 100%).

Example 10

4-{2-[5-(2-Methoxy-phenyl)-pyridin-2-yloxy]-acetylamino}-thiophene-3-carboxylic acid Step 1: 4-[2-(5-Bromo-pyridin-2-yloxy)-acetylamino]-thiophene-3-carboxylic acid methyl ester To a solution of 4-amino-thiophene-3-carboxylic acid methyl ester (0.5 g, 2.58 mmol) in dimethylformamide (25 mL) was added N-ethyldiisopropylamine (2.25 mL, 12.9 mmol), (5-bromo-pyridin-2-yloxy)-acetic acid ([79674-66-1], 0.6 g, 2.58 mmol) and HATU (Acros 365312, 1.24 g, 3.23 mmol). The reaction mixture was stirred for 2 hours at room temperature. After such time water was added to the reaction mixture until precipitation occurred (sonication was also used to ease precipitation). The precipitate was then isolated by filtration and washed with a mixture of water and ethanol (3:1) to yield the title compound as a light brown solid (0.96 g, 73%).

Mp=138-140° C., MS (m/e): 373 (M+H$^+$, 73%), 370.3 (55%), 219.1 (100%).

Step 2: 4-[2-[5-(2-Methoxy-phenyl)-pyridin-2-yloxy]-acetylamino]-thiophene-3-carboxylic acid methyl ester To a solution of 4-[2-(5-bromo-pyridin-2-yloxy)-acetylamino]-thiophene-3-carboxylic acid methyl ester (50 g, 0.135 mmol) in a mixture of tetrahydrofuran (10.5 mL) and water (2.5 mL) was added 2-methoxyphenylboronic acid (24.5 mg, 0.162 mmol) and cesium carbonate (175.3 mg, 0.54 mmol). The solution was then degassed by bubbling a flux of argon for 20 minutes before adding tetrakis(triphenylphosphine)palladium (4.24 mg, 0.0034 mmol). The reaction mixture was then stirred overnight at 80° C. under argon atmosphere before allowing to cool down to room temperature and diluting with ethyl acetate. The reaction mixture was then filtered; the filtrate was then washed twice with water and dried over sodium sulfate before being concentrated in vacuo. The residue was then purified by column chromatography (SiO$_2$, EtOAc/Heptane, 0-60%) to yield the title compound as a light yellow solid (42.5 mg, 79%).

MS (m/e): 399.1 (M+H$^+$, 100%).

Step 3: 4-{2-[5-(2-Methoxy-phenyl)-pyridin-2-yloxy]-acetylamino}-thiophene-3-carboxylic acid To 4-{2-[5-(2-methoxy-phenyl)-pyridin-2-yloxy]-acetylamino}-thiophene-3-carboxylic acid methyl ester (93 mg, 0.233 mmol) in ethanol (10 mL) was added a solution of sodium hydroxide (1N, 0.47 mL, 0.47 mmol) and the reaction was stirred at room temperature for 2 days. After such time the reaction mixture was filtered through glass wool and the filtrate was then neutralized by addition of a solution of hydrochloric acid (1N, 0.46 mL). Additional water was added to the solution (in excess of 10 mL) before the precipitate was isolated by filtration, washed with water and dried in vacuo to yield the title compound as a white solid (79 mg, 88%).

Mp=194-197° C., MS (m/e): 383.1 (M−H$^-$, 100%).

Example 11

4-{2-[5-(4-Fluoro-phenyl)-pyridin-2-yloxy]-acetylamino}-thiophene-3-carboxylic acid In analogy to Example 2, from 4-[2-(5-bromo-pyridin-2-yloxy)-acetylamino]-thiophene-3-carboxylic acid methyl ester (example 10, step 1) and 4-fluoroboronic acid was prepared 4-{2-[5-(4-fluoro-phenyl)-pyridin-2-yloxy]-acetylamino}-thiophene-3-carboxylic acid methyl ester.

MS (m/e): 387.1 (M−H$^-$, 100%).

In analogy to Example 2 (step 2), hydrolysis of 4-{2-[5-(4-fluoro-phenyl)-pyridin-2-yloxy]-acetylamino}-thiophene-3-carboxylic acid methyl ester yielded 4-{2-[5-(4-fluoro-phenyl)-pyridin-2-yloxy]-acetylamino}-thiophene-3-carboxylic acid.

MS (m/e): 371.0 (M−H$^-$, 100%).

Example 12

4-[4-(2-Chloro-phenoxy)-butyrylamino]-thiophene-3-carboxylic acid

Step 1: 4-(2-Chloro-phenoxy)-butyric acid [5057-52-3]

To a solution of sodium (405 mg, 1.08 mmol) in ethanol (11.1 mL) was added 2-chlorophenol and the reaction mixture was stirred for 5 minutes before adding dihydro-furan-2-one (1.4 g, 16.1 mmol). The reaction mixture was stirred for 5 hours at 100° C. after which time the ethanol was slowly evaporated by continuous heating to 150° C. for another 12 hours. After such time the residue was dissolved in water (7 mL) and aqueous hydrochloric acid (1N) was added until precipitation occurred. The precipitate was isolated by filtration, washed with water and dried in vacuo to yield the title compound as yellow solid (2.79 g, 80.4%).

MS (m/e): 212.9 (M−H$^-$, 100%).

Step 2: 4-(2-Chloro-phenoxy)-butyryl chloride

To 4-(2-chloro-phenoxy)-butyric acid (250 mg, 1.165 mmol) was added portion wise thionyl chloride (1.69 mL), and the reaction mixture was stirred for 3 hours at 90° C. After such time the excess of thionyl chloride was removed in vacuo to yield the crude title compound which was used in the next step without any further purification.

Step 3: 4-[4-(2-Chloro-phenoxy)-butyrylamino]-thiophene-3-carboxylic acid methyl ester To 4-amino-thiophene-3-carboxylic acid methyl ester hydrochloride (199 mg, 0.994 mmol) in dichloromethane (1.9 mL) and triethylamine (0.29 mL, 2.08 mmol), was slowly added a crude solution of 4-(2-chloro-phenoxy)-butyryl chloride (271 mg, approximately 1.16 mmol) in dichloromethane (1.9 mL). The reaction mixture was stirred for 3 hours at room temperature. The reaction mixture was then further diluted with dichloromethane (50 mL) and washed with water. The aqueous phase was then extracted with dichloromethane and the combined organic phases were dried with sodium sulfate, and concentrated in vacuo. The residue was then purified by column chromatography ($SiO_2$, Heptane/EtOAc: 0-80%) to yield the title compound as a white solid (281 mg, 80%).

MS (m/e): 354.1 (M+H$^+$, 100%).

Step 4: 4-[4-(2-Chloro-phenoxy)-butyrylamino]-thiophene-3-carboxylic acid

4-[4-(2-Chloro-phenoxy)-butyrylamino]-thiophene-3-carboxylic acid methyl ester (270 mg, 0.763 mmol) was added to a solution of lithium hydroxide monohydrate (71.1 mg, 1.68 mmol) in a mixture of tetrahydrofuran (7.4 mL) and water (7.4 mL) and the reaction mixture was stirred for 3 hours at room temperature. The tetrahydrofuran was evaporated and the solution was neutralized by addition of a solution of hydrochloric acid (1N, 0.39 mL). The precipitate was filtered, washed with water and dried in vacuo to yield the title compound as a yellow solid (218 mg, 84%).

MS (m/e): 338.1 (M−H$^-$, 100%).

Example 13

4-[4-(3-Chloro-phenoxy)-butyrylamino]-thiophene-3-carboxylic acid

In analogy to the synthesis of Example 12, 4-[4-(3-chloro-phenoxy)-butyrylamino]-thiophene-3-carboxylic acid was prepared by replacing in step 1, 2-chlorophenol by 3-chlorophenol.

MS (m/e): 338.1 (M−H$^-$, 100%).

Example 14

4-[4-(2-Fluoro-phenoxy)-butyrylamino]-thiophene-3-carboxylic acid

In analogy to the synthesis of Example 12, 4-[4-(2-fluoro-phenoxy)-butyrylamino]-thiophene-3-carboxylic acid was prepared by replacing in step 1, 2-chlorophenol by 2-fluorophenol.

MS (m/e): 322.1 (M−H$^-$, 100%).

Example 15

4-[4-(3-Fluoro-phenoxy)-butyrylamino]-thiophene-3-carboxylic acid

In analogy to the synthesis of Example 12, 4-[4-(3-fluoro-phenoxy)-butyrylamino]-thiophene-3-carboxylic acid was prepared by replacing in step 1, 2-chlorophenol by 3-fluorophenol.

MS (m/e): 322.1 (M−H$^-$, 100%).

Example 16

4-(4-Phenoxy-butyrylamino)-thiophene-3-carboxylic acid

In analogy to the synthesis of Example 12, 4-(4-phenoxy-butyrylamino)-thiophene-3-carboxylic acid was prepared by replacing in step 1, 2-chlorophenol by phenol.

MS (m/e): 322.1 (M−H$^-$, 100%).

Example 17

Rac-4-(2-Methyl-4-phenoxy-butyrylamino)-thiophene-3-carboxylic acid

In analogy to the synthesis of Example 12, rac-4-(2-methyl-4-phenoxy-butyrylamino)-thiophene-3-carboxylic acid was prepared by replacing in step 1, 2-chlorophenol and dihydro-furan-2-one by phenol and rac-3-methyl-dihydro-furan-2-one respectively.

MS (m/e): 318.1 (M−H$^-$, 100%).

Example 18

4-[2-(3,4-Dichloro-phenoxy)-acetylamino]-thiophene-3-carboxylic acid

Step 1: 4-[2-(3,4-Dichloro-phenoxy)-acetylamino]-thiophene-3-carboxylic acid methyl ester To a solution of methyl 4-(2-chloroacetamido)-3-thiophenecarboxylate ([51486-30-7], 100 mg, 0.428 mmol) in dimethylformamide (1.5 mL) was added potassium carbonate (88.7 mg, 0.642 mmol) and 3,4-dichlorophenol (83.7 mg, 0.514 mmol) and the reaction mixture was stirred at 90° C. overnight. After such time water was added. The precipitate was isolated by filtration, washed with water and dried in vacuo to yield the title compound as a white solid (108.1 mg, 70%).

Mp=179-182° C., MS (m/e): 360.1 (M−H$^-$, 100%), 358.1 (62%).

Step 2: 4-[2-(3,4-Dichloro-phenoxy)-acetylamino]-thiophene-3-carboxylic acid

To 4-[2-(3,4-dichloro-phenoxy)-acetylamino]-thiophene-3-carboxylic acid methyl ester (80 mg, 0.222 mmol) in suspension in ethanol was added an aqueous solution of sodium hydroxide (1N, 0.333 mL, 0.333 mmol) and the reaction mixture was stirred at room temperature for 48 hours. After such time the reaction mixture was filtered and the filtrate was neutralized by addition of an aqueous solution of hydrochloric acid (1N, 0.335 mL). The precipitate was then isolated by filtration, washed with water and dried in vacuo to yield the title compound as a white solid (62.1 mg, 80%).

Mp=258-264° C., MS (m/e): 344.0 (M−H$^-$, 100%).

Example 19

4-{2-[5-(2-Chloro-phenyl)-pyridin-2-yloxy]-acetylamino}-thiophene-3-carboxylic acid Step 1: 4-[2-(5-Bromo-pyridin-2-yloxy)-acetylamino]-thiophene-3-carboxylic acid methyl ester To a solution of methyl 4-amino-3-thiophenecarboxylate hydrochloride (500 mg, 2.58 mmol) in dimethylformamide (25 mL) was added N-ethyldiisopropylamine (2.26 mL, 12.9 mmol), (5-bromo-pyridin-2-yloxy)-acetic acid ([79674-66-

1], 600 mg, 2.58 mmol) and HATU (1.24 g, 3.23 mmol). The reaction mixture was allowed to stir for 2 hours at room temperature. After such time, water was added, and precipitation was eased by ultrasonication. The precipitate was isolated by filtration and washed with a mixture of water and ethanol (3:1) to yield 4-[2-(5-bromo-pyridin-2-yloxy)-acetylamino]-thiophene-3-carboxylic acid methyl ester (699 mg, 73%) as a light brown solid.

Mp=138-140° C., MS (m/e): 373.1 (73%, M+H$^+$), 370.9 (55%), 216.1 (100%), 241.1 (95%).

Step 2: 4-[2-[5-(2-Chloro-phenyl)-pyridin-2-yloxy]-acetylamino]-thiophene-3-carboxylic acid methyl ester To a solution of 4-[2-(5-bromo-pyridin-2-yloxy)-acetylamino]-thiophene-3-carboxylic acid methyl ester (100 mg, 0.269 mmol), 2-chlorophenylboronic acid (50.5 mg) and cesium carbonate (350 mg) in THF (10.5 mL) and degassed water (2.5 mL) was added tetrakis(triphenylphosphine)palladium (8.4 mg) and the reaction mixture was stirred under argon for 2 hours at 80° C. After such time water was added and the precipitate was isolated, washed with water and dried in vacuo to yield 4-{2-[5-(2-chloro-phenyl)-pyridin-2-yloxy]-acetylamino}-thiophene-3-carboxylic acid methyl ester.

Mp=151-155° C., MS (m/e): 403.3 (M+H$^+$).

Step 3: 4-[2-[5-(2-Chloro-phenyl)-pyridin-2-yloxy]-acetylamino]-thiophene-3-carboxylic acid To a suspension of 4-{2-[5-(2-chloro-phenyl)-pyridin-2-yloxy]-acetylamino}-thiophene-3-carboxylic acid methyl ester (79 mg) in ethanol (10 mL) was added a solution of sodium hydroxide (1M, 0.392 mL) and THF (8 mL) and the reaction mixture was stirred at room temperature over night. After such time the reaction mixture was acidified by addition of a solution of hydrochloric acid (1N, 0.395 mL) and then water was added. The precipitate was isolated by filtration, washed with water and dried in vacuo to yield 4-{2-[5-(2-chloro-phenyl)-pyridin-2-yloxy]-acetylamino}-thiophene-3-carboxylic acid (51 mg, 67%).

Mp=218-223° C., MS (m/e): 387.1 (M–H$^-$, 100%), 389.2 (51%).

Example 20

4-[2-(4-Cyclohexyl-phenoxy)-acetylamino]-thiophene-3-carboxylic acid

Step 1: 4-[2-(4-Cyclohexyl-phenoxy)-acetylamino]-thiophene-3-carboxylic acid methyl ester To a solution of methyl 4-(2-chloroacetamido)-3-thiophenecarboxylate ([51486-30-7], 0.1g) in dimethylformamide (1.5 mL) was added 4-cyclohexyl-phenol (0.91 mg) and potassium carbonate (89 mg). The reaction mixture was then stirred at 90° C. overnight, after what water was added yielding precipitation. The precipitate was isolated and dried in vacuo to give 4-[2-(4-cyclohexyl-phenoxy)-acetylamino]-thiophene-3-carboxylic acid methyl ester (96 mg, 60%) as a white solid.

MS (m/e): 376.3 (7%), 375.3 (25%), 374.2 (100%).

Step 2: 4-[2-(4-Cyclohexyl-phenoxy)-acetylamino]-thiophene-3-carboxylic acid

To a solution of 4-[2-(4-cyclohexyl-phenoxy)-acetylamino]-thiophene-3-carboxylic acid methyl ester (75 mg) in 2.5 mL of a mixture of THF:water (1.5:1) was added sodium hydroxide (0.442 mL, 1 M, 2.2 eq) and the reaction mixture was stirred for 24 hours at room temperature. Then the reaction mixture was acidified by addition of a solution of aqueous HCl (0.442 mL, 1N, 2.2 eq). The precipitate was isolated, washed with water and dried in vacuo to yield 4-[2-(4-cyclohexyl-phenoxy)-acetylamino]-thiophene-3-carboxylic acid (51 mg, 71%) as a white solid.

MS (m/e): 359.2 (M–H$^-$, 29%), 358.2 (100%), 300.2 (10%).

Example 21

4-[2-(4-Cyclopentyl-phenoxy)-acetylamino]-thiophene-3-carboxylic acid

In analogy to Example 20 (step 1), from 4-cyclopentyl-phenol and methyl 4-(2-chloroacetamido)-3-thiophenecarboxylate ([51486-30-7]) was prepared 4-[2-(4-cyclopentyl-phenoxy)-acetylamino]-thiophene-3-carboxylic acid methyl ester.

MS (m/e): 363.8 (M+H$^+$, 8%), 361.3 (20%), 360.1 (100%).

In analogy to Example 20 (step 2), 4-[2-(4-cyclopentyl-phenoxy)-acetylamino]-thiophene-3-carboxylic acid methyl ester was hydrolysed to 4-[2-(4-cyclopentyl-phenoxy)-acetylamino]-thiophene-3-carboxylic acid.

MS (m/e): 346.2 (7%), 345.1 (14%), 344.2 (100%).

Example 22

4-[2-(4-Isopropyl-phenoxy)-acetylamino]-thiophene-3-carboxylic acid

In analogy to Example 20 (step 1), from 4-isopropyl-phenol and methyl 4-(2-chloroacetamido)-3-thiophenecarboxylate ([51486-30-7]) was prepared 4-[2-(4-isopropyl-phenoxy)-acetylamino]-thiophene-3-carboxylic acid methyl ester.

MS (m/e): 335.3 (17%), 334.2 (83%).

In analogy to Example 20 (step 2), 4-[2-(4-isopropyl-phenoxy)-acetylamino]-thiophene-3-carboxylic acid methyl ester was hydrolysed to 4-[2-(4-isopropyl-phenoxy)-acetylamino]-thiophene-3-carboxylic acid.

MS (m/e): 320.2 (7%), 319.1 (10%), 318.1 (100%).

Example 23

4-[2-(4-tert-Butyl-phenoxy)-acetylamino]-thiophene-3-carboxylic acid

In analogy to Example 20 (step 1) from 4-tert-butyl-phenol and methyl 4-(2-chloroacetamido)-3-thiophenecarboxylate ([51486-30-7]) was prepared 4-[2-(4-tert-butyl-phenoxy)-acetylamino]-thiophene-3-carboxylic acid methyl ester.

MS (m/e): 349.3 (17%), 348.2 (84%).

In analogy to Example 20 (step 2), 4-[2-(4-tert-butyl-phenoxy)-acetylamino]-thiophene-3-carboxylic acid methyl ester was hydrolyzed to 4-[2-(4-tert-butyl-phenoxy)-acetylamino]-thiophene-3-carboxylic acid.

MS (m/e): 334.2 (10%), 333.2 (32%), 332.3 (100%).

Example 24 rac-4-[2-(4-sec-Butyl-phenoxy)-acetylamino]-thiophene-3-carboxylic acid

In analogy to Example 20 (step 1) from 4-sec-butyl-phenol and methyl 4-(2-chloroacetamido)-3-thiophenecarboxylate ([51486-30-7]) was prepared rac-4-[2-(4-sec-butyl-phenoxy)-acetylamino]-thiophene-3-carboxylic acid methyl ester.

MS (m/e): 350.5 (5%), 349.3 (16%), 348.2 (83%).

In analogy to Example 20 (step 2), rac-4-[2-(4-sec-butyl-phenoxy)-acetylamino]-thiophene-3-carboxylic acid methyl ester was hydrolyzed to rac-4-[2-(4-sec-butyl-phenoxy)-acetylamino]-thiophene-3-carboxylic acid.

MS (m/e): 334.2 (9%), 333.3 (33%), 332.2 (100%).

Example 25

4-{2-[5-(2-Fluoro-phenyl)-pyridin-2-yloxy]-acetylamino}-thiophene-3-carboxylic acid In analogy to Example 19 (step 2) from 2-fluorophenyl boronic acid and 4-[2-(5-bromo-pyridin-2-yloxy)-acetylamino]-thiophene-3-carboxylic acid methyl ester was prepared 4-{2-[5-(2-fluoro-phenyl)-pyridin-2-yloxy]-acetylamino}-thiophene-3-carboxylic acid methyl ester.

MS (m/e): 387.1 (M+H$^+$).

In analogy to Example 19 (step 3) 4-{2-[5-(2-fluoro-phenyl)-pyridin-2-yloxy]-acetylamino}-thiophene-3-carboxylic acid methyl ester was hydrolyzed into 4-{2-[5-(2-fluoro-phenyl)-pyridin-2-yloxy]-acetylamino}-thiophene-3-carboxylic acid.

MS (m/e): 371.0 (M+H$^-$).

Example 26

4-[2-(4-Pyrimidin-2-yl-phenoxy)-acetylamino]-thiophene-3-carboxylic acid

Step 1: 4-[2-(4-Pyrimidin-2-yl-phenoxy)-acetylamino]-thiophene-3-carboxylic acid methyl ester To 4-[2-(4-Iodo-phenoxy)-acetylamino]-thiophene-3-carboxylic acid methyl ester (77.6 mg) in DMF (1 mL) was added 2-(tributylstannyl)pyrimidine (74.1 mg), tris(dibenzylideneacetone)-di-Palladium, triphenylarsine (27 mg) and copper (I) iodide (3.2 mg) and the reaction mixture was stirred at 90° C. overnight. The reaction mixture was then allowed to cool to room temperature and was concentrated in vacuo. To the residue was then added ethylacetate (4 mL) and an aqueous solution of potassium fluoride (30%) and the mixture was stirred rigorously for one hour. Then the solid was filtered off and the biphasic filtrate was separated. The organic layer was dried with sodium sulfate and concentrated in vacuo. The residue was then purified by column chromatography to yield the title compound (41 mg, 59%).

MS (m/e): 369.9 (M+H$^+$).

Step 2: 4-[2-(4-Pyrimidin-2-yl-phenoxy)-acetylamino]-thiophene-3-carboxylic acid To 4-[2-(4-Pyrimidin-2-yl-phenoxy)-acetylamino]-thiophene-3-carboxylic acid methyl ester (41 mg) in a 1:1 mixture of THF and water (2.25 mL) was added lithium hydroxide monohydrate and the reaction mixture was stirred for 20 hours at room temperature. After such time the THF was evaporated off in vacuo and the remaining aqueous phase was neutralized by addition of a 1N HCl solution. The resulting precipitate was then isolated by filtration, washed with water, and dried in vacuo to yield the title compound as a light yellow solid. MS (m/e): 354.1 (M+H$^-$).

Example 27

4-[2-(4-Pyrazin-2-yl-phenoxy)-acetylamino]-thiophene-3-carboxylic acid

In analogy to Example 26, the title compound was prepared using 2-(tributylstannyl)pyrazin instead of 2-(tributylstannyl)pyrimidine. MS (m/e): 354.0 (M–H).

Example 28

4-[2-(4-Pyridin-2-yl-phenoxy)-acetylamino]-thiophene-3-carboxylic acid

In analogy to Example 26, the title compound was prepared using 2-(tributylstannyl)pyridin instead of 2-(tributylstannyl)pyrimidine. MS (m/e): 353.3 (M–H).

Example 29

4-[2-(4-Pyridin-3-yl-phenoxy)-acetylamino]-thiophene-3-carboxylic acid

In analogy to Example 26, the title compound was prepared using 3-(tributylstannyl)pyridin instead of 2-(tributylstannyl)pyrimidine. MS (m/e): 353.0 (M–H).

Example 30

4-[2-(4-Pyridin-4-yl-phenoxy)-acetylamino]-thiophene-3-carboxylic acid

In analogy to Example 26, the title compound was prepared using 4-(tributylstannyl)pyridin instead of 2-(tributylstannyl)pyrimidine. MS (m/e): 353.0 (M–H).

Example 31

4-[2-(4-Chloro-phenoxy)-acetylamino]-thiophene-3-carboxylic acid

In analogy to Example 2, the title compound was prepared using 4-chlorophenol. MS (m/e): 310.2 (M+H$^+$).

Example 32

4-[2-(3,5-dichloro-phenoxy)-acetylamino]-thiophene-3-carboxylic acid

In analogy to Example 2, the title compound was prepared using 3,5-dichlorophenol. MS (m/e): 344.0 (M+H$^+$).

Example 33

4-[2-(3-Chloro-phenoxy)-acetylamino]-thiophene-3-carboxylic acid

In analogy to Example 2, the title compound was prepared using 3-chlorophenol. MS (m/e): 310.2 (M+H$^+$).

Example 34

4-(2-m-Tolyloxy-acetylamino)-thiophene-3-carboxylic acid

In analogy to Example 2, the title compound was prepared using 3-methylphenol. MS (m/e): 290.1 (M–H).

Example 35

4-[2-(3-Ethyl-phenoxy)-acetylamino]-thiophene-3-carboxylic acid

In analogy to Example 2, the title compound was prepared using 3-ethylphenol. MS (m/e): 304.1 (M–H).

Example 36

4-[2-(3-Nitro-phenoxy)-acetylamino]-thiophene-3-carboxylic acid

In analogy to Example 2, the title compound was prepared using 3-nitrophenol. MS (m/e): 304.1 (M−H).

Example 37

4-[2-(3-Ethoxy-phenoxy)-acetylamino]-thiophene-3-carboxylic acid

In analogy to Example 2, the title compound was prepared using 3-ethoxyphenol. MS (m/e): 320.2 (M−H).

Example 38

4-[2-(3-Ethynyl-phenoxy)-acetylamino]-thiophene-3-carboxylic acid

In analogy to Example 2, the title compound was prepared using 3-ethynylphenol. MS (m/e): 302.1 (M+H$^+$).

Example 39

4-[2-(Biphenyl-3-yloxy)-acetylamino]-thiophene-3-carboxylic acid

In analogy to Example 2, the title compound was prepared using biphenyl-3-ol. MS (m/e): 354.1 (M+H+).

Example 40

4-[2-(3-Chloro-4cyano-phenoxy)-acetylamino]-thiophene-3-carboxylic acid

In analogy to Example 2, the title compound was prepared using 3-chloro-4-cyano phenol. MS (m/e): 335.2 (M−H).

Example 41

4-[2-(3-Trifluoromethyl-phenoxy)-acetylamino]-thiophene-3-carboxylic acid

In analogy to Example 2, the title compound was prepared using 3-trifluoromethyl phenol. MS (m/e): 344.1 (M−H).

Example 42

4-[2-(3-Chloro-4-methyl-phenoxy)-acetylamino]-thiophene-3-carboxylic acid

In analogy to Example 2, the title compound was prepared using 3-chloro-4-methyl phenol. MS (m/e): 324.2 (M−H).

Example 43

4-[2-(4-Chloro-3-fluoro-phenoxy)-acetylamino]-thiophene-3-carboxylic acid

In analogy to Example 2, the title compound was prepared using 4-chloro-3-fluoro phenol. MS (m/e): 328.1 (M−H).

Example 44

4-[2-(4-Chloro-3-trifluoromethyl-phenoxy)-acetylamino]-thiophene-3-carboxylic acid In analogy to Example 2, the title compound was prepared using 4-chloro-3-trifluoromethyl phenol. MS (m/e): 378.2 (M−H).

Example 45

4-[2-(2-Fluoro-5-trifluoromethyl-phenoxy)-acetylamino]-thiophene-3-carboxylic acid In analogy to Example 2, the title compound was prepared using 2-fluoro-3-trifluoromethyl phenol. MS (m/e): 362.2 (M−H).

Example 46

4-[2-(3-Fluoro-5-trifluoromethyl-phenoxy)-acetylamino]-thiophene-3-carboxylic acid In analogy to Example 2, the title compound was prepared using 3-fluoro-3-trifluoromethyl phenol. MS (m/e): 362.0 (M−H).

Example 47

4-[2-(3,5-Difluoro-phenoxy)-acetylamino]-thiophene-3-carboxylic acid

In analogy to Example 2, the title compound was prepared using 3,5-difluoro phenol. MS (m/e): 312.1(M−H).

Example 48

4-[2-(4-Trifluoromethoxy-phenoxy)-acetylamino]-thiophene-3-carboxylic acid

In analogy to Example 2, the title compound was prepared using 4-trifluoromethoxy phenol. MS (m/e): 360.1(M−H).

Example 49

4-[2-(4-Trifluoromethoxy-phenoxy)-acetylamino]-thiophene-3-carboxylic acid

In analogy to Example 2, the title compound was prepared using 4-trifluoromethoxy phenol. MS (m/e): 412.1(M−H).

Example 50

4-[2-(3-Chloro-5-fluoro-phenoxy)-acetylamino]-thiophene-3-carboxylic acid

In analogy to Example 2, the title compound was prepared using 3-chloro-5-fluoro phenol. MS (m/e): 328.1 (M−H).

Example 51

4-[2-(3,5-Dibromo-phenoxy)-acetylamino]-thiophene-3-carboxylic acid

In analogy to Example 2, the title compound was prepared using 3,5-dibromo phenol. MS (m/e): 433.9 (M−H).

Example 52

4-[2-(3,5-Dichloro-phenoxy)-acetylamino]-thiophene-3-carboxylic acid

In analogy to Example 2, the title compound was prepared using 3,5-dichloro phenol. MS (m/e): 343.1 (M−H).

Example 53

4-[2-(2-tert-Butyl-pyrimidin)-acetylamino]-thiophene-3-carboxylic acid

In analogy to Example 2, the tide compound was prepared using 2-tert-pyrimidin-5-ol [85929-96-0]. MS (m/e): 334.3 (M−H).

Example 54

4-[2-(4'-Fluoro-biphenyl-4-yloxy)-acetylamino]5-methyl-thiophene-3-carboxylic acid In analogy to Example 2, the title compound was prepared using 4-(2-chloro-acetylamino)-5-methyl-thiophene-3-carboxylic acid methyl ester [23964-99-0] and 4'-fluoro-biphenyl-4-ol. MS (m/e): 384.0 (M−H).

Example 55

Rac-4-[2-(3,4-Dichloro-phenoxy)-propionylamino]-thiophene-3-carboxylic acid

First step: rac-4-(2-Chloro-propionylamino)-thiophene-3-carboxylic acid methyl ester To a suspension of 4-amino-thiophene-3-carboxylic acid methyl ester (2.0g) in dichloromethane (25 mL) was added 2-chloropropionyl chloride (1.13 mL). The reaction mixture was then cooled down to −15° C. and a solution of triethylamine (3.2 mL) in dichloromethane (5 mL) was slowly added over 30 minutes. After such time the reaction mixture was allowed to warm up to room temperature, and the solution was washed twice with water, dried over sodium sulfate and then concentrated in vacuo. The residue was purified by column chromatography to yield the title compound as a light yellow solid (2.1g, 82%). MS (EI): 247.0.

Following steps: rac-4[-2-(3,4-Dichloro-phenoxy)-propionylamino]-thiophene-3-carboxylic acid In analogy to Example 2, the title compound was prepared using rac-4-(2-chloro-propionylamino)-thiophene-3-carboxylic acid methyl ester and 3,4-dichlorophenol. MS (m/e): 360.0 (M−H).

Example 56

Rac-4-[2-(4'-Fluoro-biphenyl-4-yloxy)-propionylamino]-thiophene-3-carboxylic acid In analogy to Example 2, the title compound was prepared using rac-4-(2-chloro-propionylamino)-thiophene-3-carboxylic acid methyl ester and 4'-fluoro-biphenyl-4-ol. MS (m/e): 384.1 (M−H).

Example 57

Rac-4-[2-(4-tertButyl-phenoxy)-propionylamino]-thiophene-3-carboxylic acid

In analogy to Example 2, the title compound was prepared using rac-4-(2-chloro-propionylamino)-thiophene-3-carboxylic acid methyl ester and 4-tert-butylphenol. MS (m/e): 346.2 (M−H).

Example 58

Rac-4-[2-Fluoro-2-(4'-fluoro-biphenyl-4-yloxy)-acetylamino]-thiophene-3-carboxylic acid Step 1: 4-(2-Chloro-2-fluoro-acetylamino)-thiophene-3-carboxylic acid methyl ester To a suspension of 4-amino-thiophene-3-carboxylic acid methyl ester (2 g) in dichloromethane (25 mL) was added chlorofluoroacetyl chloride (1.16 mL) and the reaction mixture was stirred to −15° C. Then a solution of triethylamine (3.2 mL) in dichloromethane (5 mL) was added slowly to the cold reaction mixture which was then allowed to warm up and stirred at room temperature for one hour. The reaction mixture was then diluted with further methylene chloride and washed several times with water, dried with sodium sulfate and concentrated in vacuo. The residue was purified by column chromatography to yield the title compound as a light yellow solid. MS (EI): 251.1; mp=51-54° C.

Steps 2 and 3: Rac-4-[2-Fluoro-2-(4'-fluoro-biphenyl-4-yloxy)-acetylamino]-thiophene-3-carboxylic acid In analogy to Example 2, the title compound was prepared using 4-(2-chloro-2-fluoro-acetylamino)-thiophene-3-carboxylic acid methyl ester and 4-fluoro-4'-hydroxybiphenyl. MS (m/e): 388.2 (M−H).

Example 59

Rac-4-[2-(4-tert-Butyl-phenoxy)-2-fluoro-acetylamino]-thiophene-3-carboxylic acid In analogy to Example 58, the title compound was prepared using 4-(2-chloro-2-fluoro-acetylamino)-thiophene-3-carboxylic acid methyl ester and 4-tert-butylphenol. MS (m/e): 350.3 (M−H).

Example 60

Rac-4-[2-(3,4-Dichloro-phenoxy)-2-fluoro-acetylamino]-thiophene-3-carboxylic acid In analogy to Example 58, the title compound was prepared using 4-(2-chloro-2-fluoro-acetylamino)-thiophene-3-carboxylic acid methyl ester and 3,4-dichlorophenol. MS (m/e): 362.0 (M−H).

Example 61

Rac-4-[2,2-Difluoro-2-(4'-fluoro-biphenyl-4-yloxy)-acetylamino]-thiophene-3-carboxylic acid In analogy to Example 58, the title compound was prepared using 4-amino-thiophene-3-carboxylic acid methyl ester, chlorodifluoroacetyl chloride and 4-fluoro-4'-hydroxybiphenyl. MS (m/e): 406.1 (M−H).

Example 62

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |

-continued

| Ingredients | Per tablet | |
|---|---|---|
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcristalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example 63

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 64

Injection solutions can have the following composition:

| Compound of formula (I) | 3.0 mg |
|---|---|
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example 65

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |

-continued

| Titanium dioxide | 0.4 mg |
|---|---|
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 66

Sachets containing the following ingredients can be manufactured in a conventional manner:

| Compound of formula (I) | 50.0 mg |
|---|---|
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

It is to be understood that the invention is not limited to the particular embodiments of the invention described above, as variations of the particular embodiments may be made and still fall within the scope of the appended claims.

What is claimed is:

1. A compound of formula (I):

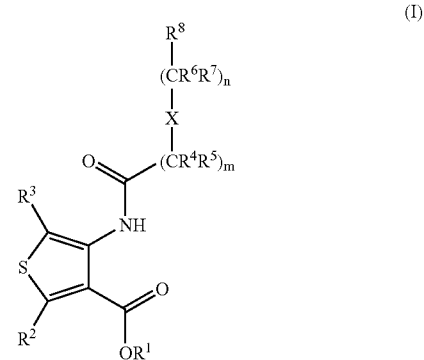

wherein

X is O;

$R^1$ is hydrogen or lower-alkyl;

$R^2$ is hydrogen, halogen, lower-alkyl or fluoro-lower-alkyl;

$R^3$ is hydrogen, halogen, lower-alkyl or fluoro-lower-alkyl;

$R^4$, $R^5$, $R^6$ and $R^7$ independently from each other are hydrogen, halogen, lower-alkyl, lower-alkoxy, fluoro-lower-alkyl or fluoro-lower-alkoxy, or $R^4$ and $R^5$ are bound together to form a cycloalkyl together with the carbon atom to which they are attached and
—$R^4$—$R^5$— is —$(CH_2)_{2-6}$—, or $R^6$ and $R^7$ are bound together to form a cycloalkyl together with the carbon atom to which they are attached and —$R^6$—$R^7$— is —$(CH_2)_{2-6}$—;

or;

R⁴ and R⁶ are bound together to form a ring and —R⁴—R⁶— is —(CH₂)₂₋₆—;

R⁸ is aryl or heteroaryl, which aryl or heteroaryl is optionally substituted with 1 to 3 substituents selected from the group consisting of halogen, lower-alkyl, hydroxy-lower-alkyl, lower-alkoxy, fluoro-lower-alkoxy, carboxy, carboxy-lower-alkyl, lower-alkoxy-carbonyl, lower-alkoxy-carbonyl-lower-alkyl, R¹⁰R¹¹NC(O), R¹⁰R¹¹NC(O)lower-alkyl, fluoro-lower-alkyl, R¹⁰R¹¹N-lower-alkyl, lower-alkyl-SO₂, lower-alkyl-SO₂O, lower-alkyl-SO₂—NR¹⁰, R¹⁰R¹¹NSO₂, cyano, NO₂, cycloalkyl, lower-alkoxy-lower-alkyl, lower-alkenyl, lower-alkinyl, fluoro-lower-alkoxy-lower-alkyl, cyano-lower-alkyl, phenyl and heteroaryl, which phenyl or heteroaryl is optionally substituted with 1 to 3 substituents selected from the group consisting of halogen, lower-alkyl, lower-alkoxy, lower-alkyl-C(O) and lower-alkyl-C(O)N(R¹⁰);

R⁹ is hydrogen, lower-alkyl or fluoro-lower-alkyl;

R¹⁰ and R¹¹ independently from each other are hydrogen or lower-alkyl;

m is 0, 1, 2 or 3;

n is 0, 1, 2 or 3;

or a pharmaceutically acceptable salt or a pharmaceutically acceptable ester thereof, with the proviso that the compound of formula (I) is not 2-methyl-4-[[(phenylmethoxy)carbonyl]amino]-3-thiophenecarboxylic acid methyl ester, 4-benzoxycarbonylamino-2-methylthiophen-3-carboxylic acid methyl ester, 4-methoxycarbonylamino-2-methylthiophen-3-carboxylic acid methyl ester, 3-(naphth-2-yl)-but-2-enoic acid-N-(3-carboxy-thiophen-4-yl)-amide or 3-(naphth-2-yl)but-2-enoic acid-N-(3-methoxycarbonyl-thiophen-4-yl), and with the proviso that if both m and n are 0 and R¹ is methyl, then R⁸ is not nitro-phenyl.

2. The compound according to claim 1, wherein R⁴, R⁵, R⁶ and R⁷ independently from each other are hydrogen, lower-alkyl, lower-alkoxy, fluoro-lower-alkyl or fluoro-lower-alkoxy, or R⁴ and R⁵ are bound together to form a cycloalkyl together with the carbon atom to which they are attached and —R⁴—R⁵— is —(CH₂)₂₋₆—, or R⁶ and R⁷ are bound together to form a cycloalkyl together with the carbon atom to which they are attached and —R⁶—R⁷— is —(CH₂)₂₋₆—; and R⁸ is aryl or heteroaryl, which aryl or heteroaryl is optionally substituted with 1 to 3 substituents selected from the group consisting of halogen, lower-alkyl, hydroxy-lower-alkyl, lower-alkoxy, fluoro-lower-alkoxy, carboxy, carboxy-lower-alkyl, lower-alkoxy-carbonyl, lower-alkoxy-carbonyl-lower-alkyl, R¹⁰R¹¹NC(O), R¹⁰R¹¹NC(O)-lower-alkyl, fluoro-lower-alkyl, R¹⁰R¹¹N-lower-alkyl, lower-alkyl-SO₂, lower-alkyl-SO₂O, lower-alkyl-SO₂—NR¹⁰, R¹⁰R¹¹NSO₂, cyano, cycloalkyl, lower-alkoxy-lower-alkyl, lower-alkenyl, lower-alkinyl, fluoro-lower-alkoxy-lower-alkyl, cyano-lower-alkyl, phenyl and heteroaryl, which phenyl or heteroaryl is optionally substituted with 1 to 3 substituents selected from the group consisting of halogen, lower-alkyl, lower-alkoxy, lower-alkyl-C(O) and lower-alkyl-C(O)N(R¹⁰), wherein R¹⁰ and R¹¹ are as defined in claim 1.

3. The compound according to claim 1, wherein R¹ is hydrogen.

4. The compound according to claim 1, wherein R² is hydrogen.

5. The compound according to claim 1, wherein R³ is hydrogen or lower-alkyl.

6. The compound according to claim 1, wherein R³ is hydrogen.

7. The compound according to claim 1, wherein R⁴, R⁵, R⁶ and R⁷ independently from each other are hydrogen, halogen or lower-alkyl.

8. The compound according to claim 1, wherein R⁴, R⁵, R⁶ and R⁷ independently from each other are hydrogen or lower-alkyl.

9. The compound according to claim 1, wherein R⁴, R⁵, R⁶ and R⁷ independently from each other are hydrogen or methyl.

10. The compound according to claim 1, wherein R⁸ is aryl or heteroaryl, which aryl or heteroaryl is optionally substituted with 1 to 3 substituents selected from the group consisting of halogen, lower-alkyl, lower-alkoxy, fluoro-lower-alkoxy, fluoro-lower-alkyl, cyano, NO₂, cycloalkyl, pyrimidinyl, pyrazinyl, pyridinyl and phenyl, which phenyl is optionally substituted with 1 to 3 substituents selected from the group consisting of halogen, lower-alkyl, lower-alkoxy, lower-alkyl-C(O) and lower-alkyl-C(O)N(R¹⁰), and R¹⁰ is as defined in claim 1.

11. The compound according to claim 1, wherein R⁸ is aryl or heteroaryl, which aryl or heteroaryl is optionally substituted with 1 to 3 substituents selected from the group consisting of halogen, lower-alkyl, cycloalkyl and phenyl, which phenyl is optionally substituted with 1 to 3 substituents selected from the group consisting of halogen, lower-alkyl, lower-alkoxy, lower-alkyl-C(O) and lower-alkyl-C(O)N(R¹⁰).

12. The compound according to claim 1, wherein R⁸ is phenyl or pyridinyl, which phenyl or pyridinyl is optionally substituted with 1 to 3 substituents selected from the group consisting of halogen, lower-alkyl, cycloalkyl and phenyl, which phenyl is optionally substituted with 1 to 3 substituents selected from the group consisting of halogen and lower-alkoxy.

13. The compound according to claim 1, wherein R⁸ is 4'-fluoro-biphenyl-4-yl, biphenyl-4-yl, 2'-methoxy-biphenyl-4-yl, 5-(4-fluoro-phenyl)-pyridin-2-yl, 2-chloro-phenyl, phenyl, 3,4-dichloro-phenyl, 4-cyclopentyl-phenyl, 4-tert-butyl-phenyl or 5-(2-fluoro-phenyl)-pyridin-2-yl.

14. The compound according to claim 1, wherein R⁸ is 4-pyrimidin-2-yl-phenyl, 4-pyrazin-2-yl-phenyl, 4-pyridin-2-yl-phenyl, 4-pyridin-3-yl-phenyl or biphenyl-3-yl.

15. The compound according to claim 1, wherein m is 1, 2 or 3.

16. The compound according to claim 1, wherein m is 1 or 3.

17. The compound according to claim 1, wherein n is 0.

18. The compound according to claim 1, wherein R⁹ is hydrogen.

19. The compound according to claim 1, wherein R¹⁰ and R¹¹ are hydrogen.

20. The compound according to claim 1, wherein, if R¹ is hydrogen or methyl, R² and R³ are hydrogen, m is 1, R⁴ and R⁵ are hydrogen, X is O, n is 0, then R⁸ is not biphenyl or phenyl-pyridazinyl.

21. The compound according to claim 1, selected from the group consisting of
- 4-[2-(4'-Fluoro-biphenyl-4-yloxy)-acetylamino]-thiophene-3-carboxylic acid,
- 4-[2-(Biphenyl-4-yloxy)-acetylamino]-thiophene-3-carboxylic acid,
- 4-[2-(2'-Methoxy-biphenyl-4-yloxy)-acetylamino]-thiophene-3-carboxylic acid,
- 4-[2-(3'-Chloro-biphenyl-4-yloxy)-acetylamino]-thiophene-3-carboxylic acid,
- 4-[2-(2'-Methyl-biphenyl-4-yloxy)-acetylamino]-thiophene-3-carboxylic acid,
- 4-[2-(3'-Acetylamino-biphenyl-4-yloxy)-acetylamino]-thiophene-3-carboxylic acid,
- 4-[2-(3'-Methoxy-biphenyl-4-yloxy)-acetylamino]-thiophene-3-carboxylic acid,
- 4-[2-(3'-Acetyl-biphenyl-4-yloxy)-acetylamino]-thiophene-3-carboxylic acid, 4-{2-[5-(2-Methoxy-phenyl)-pyridin-2-yloxy]-acetylamino}-thiophene-3-carboxylic acid,
4-{2-[5-(4-Fluoro-phenyl)-pyridin-2-yloxy]-acetylamino}-thiophene-3-carboxylic acid,
4-[4-(2-Chloro-phenoxy)-butyrylamino]-thiophene-3-carboxylic acid,
4-[4-(3-Chloro-phenoxy)-butyrylamino]-thiophene-3-carboxylic acid,
4-[4-(2-Fluoro-phenoxy)-butyrylamino]-thiophene-3-carboxylic acid,
4-[4-(3-Fluoro-phenoxy)-butyrylamino]-thiophene-3-carboxylic acid,
4-(4-Phenoxy-butyrylamino)-thiophene-3-carboxylic acid,
4-(2-Methyl-4-phenoxy-butyrylamino)-thiophene-3-carboxylic acid,
4-[2-(3,4-Dichloro-phenoxy)-acetylamino]-thiophene-3-carboxylic acid,
4-{2-[5-(2-Chloro-phenyl)-pyridin-2-yloxy]-acetylamino}-thiophene-3-carboxylic acid,
4-[2-(4-Cyclohexyl-phenoxy)-acetylamino]-thiophene-3-carboxylic acid,
4-[2-(4-Cyclopentyl-phenoxy)-acetylamino]-thiophene-3-carboxylic acid,
4-[2-(4-Isopropyl-phenoxy)-acetylamino]-thiophene-3-carboxylic acid,
4-[2-(4-tert-Butyl-phenoxy)-acetylamino]-thiophene-3-carboxylic acid,
4-[2-(4-sec-Butyl-phenoxy)-acetylamino]-thiophene-3-carboxylic acid, and
4-{2-[5-(2-Fluoro-phenyl)-pyridin-2-yloxy]-acetylamino}-thiophene-3-carboxylic acid,
or a pharmaceutically acceptable salt or ester thereof.

22. The compound according to claim 1, selected from the group consisting of
4-[2-(4'-Fluoro-biphenyl-4-yloxy)-acetylamino]-thiophene-3-carboxylic acid;
4-[2-(Biphenyl-4-yloxy)-acetylamino]-thiophene-3-carboxylic acid;
4-[2-(2'-Methoxy-biphenyl-4-yloxy)-acetylamino]-thiophene-3-carboxylic acid;
4-{2-[5-(4-Fluoro-phenyl)-pyridin-2-yloxy]-acetylamino}-thiophene-3-carboxylic acid;
4-[4-(2-Chloro-phenoxy)-butyrylamino]-thiophene-3-carboxylic acid;
4-(2-Methyl-4-phenoxy-butyrylamino)-thiophene-3-carboxylic acid;
4-[2-(3,4-Dichloro-phenoxy)-acetylamino]-thiophene-3-carboxylic acid;
4-[2-(4-Cyclopentyl-phenoxy)-acetylamino]-thiophene-3-carboxylic acid;
4-[2-(4-tert-Butyl-phenoxy)-acetylamino]-thiophene-3-carboxylic acid; and
4-{2-[5-(2-Fluoro-phenyl)-pyridin-2-yloxy]-acetylamino}-thiophene-3-carboxylic acid;
or a pharmaceutically acceptable salt or ester thereof.

23. The compound according to claim 1, selected from the group consisting of
4-[2-(4-Pyrimidin-2-yl-phenoxy)-acetylamino]-thiophene-3-carboxylic acid,
4-[2-(4-Pyrazin-2-yl-phenoxy)-acetylamino]-thiophene-3-carboxylic acid,
4-[2-(4-Pyridin-2-yl-phenoxy)-acetylamino]-thiophene-3-carboxylic acid,
4-[2-(4-Pyridin-3-yl-phenoxy)-acetylamino]-thiophene-3-carboxylic acid,
4-[2-(4-Pyridin-4-yl-phenoxy)-acetylamino]-thiophene-3-carboxylic acid,
4-[2-(4-Chloro-phenoxy)-acetylamino]-thiophene-3-carboxylic acid,
4-[2-(3,5-Dichloro-phenoxy)-acetylamino]-thiophene-3-carboxylic acid,
4-[2-(3-Chloro-phenoxy)-acetylamino]-thiophene-3-carboxylic acid,
4-(2-m-Tolyloxy-acetylamino)-thiophene-3-carboxylic acid,
4-[2-(3-Ethyl-phenoxy)-acetylamino]-thiophene-3-carboxylic acid,
4-[2-(3-Nitro-phenoxy)-acetylamino]-thiophene-3-carboxylic acid,
4-[2-(3-Ethoxy-phenoxy)-acetylamino]-thiophene-3-carboxylic acid,
4-[2-(3-Ethynyl-phenoxy)-acetylamino]-thiophene-3-carboxylic acid,
4-[2-(Biphenyl-3-yloxy)-acetylamino]-thiophene-3-carboxylic acid,
4-[2-(3-Chloro-4-cyano-phenoxy)-acetylamino]-thiophene-3-carboxylic acid,
4-[2-(3-Trifluoromethyl-phenoxy)-acetylamino]-thiophene-3-carboxylic acid,
4-[2-(3-Chloro-4-methyl-phenoxy)-acetylamino]-thiophene-3-carboxylic acid,
4-[2-(4-Chloro-3-fluoro-phenoxy)-acetylamino]-thiophene-3-carboxylic acid,
4-[2-(4-Chloro-3-trifluoromethyl-phenoxy)-acetylamino]-thiophene-3-carboxylic acid,
4-[2-(2-Fluoro-5-trifluoromethyl-phenoxy)-acetylamino]-thiophene-3-carboxylic acid,
4-[2-(3-Fluoro-5-trifluoromethyl-phenoxy)-acetylamino]-thiophene-3-carboxylic acid,
4-[2-(4-Trifluoromethoxy-phenoxy)-acetylamino]-thiophene-3-carboxylic acid,
4-[2-(3,5-Bis-trifluoromethyl-phenoxy)-acetylamino]-thiophene-3-carboxylic acid,
4-[2-(3-Chloro-5-fluoro-phenoxy)-acetylamino]-thiophene-3-carboxylic acid,
4-[2-(3,5-Dibromo-phenoxy)-acetylamino]-thiophene-3-carboxylic acid,
4-[2-(3,5-Dichloro-phenylamino)-acetylamino]-thiophene-3-carboxylic acid,
4-[2-(2-tert-Butyl-pyrimidin-5-yloxy)-acetylamino]-thiophene-3-carboxylic acid,
4-[2-(4'-Fluoro-biphenyl-4-yloxy)-acetylamino]-5-methyl-thiophene-3-carboxylic acid,
4-[2-(3,4-Dichloro-phenoxy)-propionylamino]-thiophene-3-carboxylic acid,
4-[2-(4'-Fluoro-biphenyl-4-yloxy)-propionylamino]-thiophene-3-carboxylic acid,
4-[2-(4-tert-Butyl-phenoxy)-propionylamino]-thiophene-3-carboxylic acid,
4-[2-Fluoro-2-(4'-fluoro-biphenyl-4-yloxy)-acetylamino]-thiophene-3-carboxylic acid,
4-[2-(4-tert-Butyl-phenoxy)-2-fluoro-acetylamino]-thiophene-3-carboxylic acid,
4-[2-(3,4-Dichloro-phenoxy)-2-fluoro-acetylamino]-thiophene-3-carboxylic acid, and
4-[2,2-Difluoro-2-(4'-fluoro-biphenyl-4-yloxy)-acetylamino]-thiophene-3-carboxylic acid,
or a pharmaceutically acceptable salt or ester thereof.

24. The compound according to claim 1, selected from the group consisting of
4-[2-(4-Pyrimidin-2-yl-phenoxy)-acetylamino]-thiophene-3-carboxylic acid,
4-[2-(4-Pyrazin-2-yl-phenoxy)-acetylamino]-thiophene-3-carboxylic acid,
4-[2-(4-Pyridin-2-yl-phenoxy)-acetylamino]-thiophene-3-carboxylic acid,
4-[2-(4-Pyridin-4-yl-phenoxy)-acetylamino]-thiophene-3-carboxylic acid, 4-[2-(Biphenyl-3-yloxy)-acetylamino]-thiophene-3-carboxylic acid, 4-[2-(4-tert-Butyl-phenoxy)-2-fluoro-acetylamino]-thiophene-3-carboxylic acid, and 4-[2,2-Difluoro-2-(4'-fluoro-biphenyl-4-yloxy)-acetylamino]-thiophene-3-carboxylic acid or a pharmaceutically acceptable salt or ester thereof.

25. A process for the manufacture of compounds of formula (I) according to claim 1, comprising the steps of:

a) reacting a compound of formula (II)

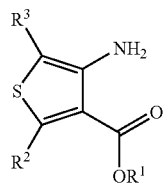

(II)

with a compound of formula (III),

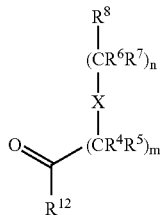

(III)

wherein $R^1$, $R^2$, $R^3$, $R^{4,\ R5}$, $R^6$, $R^7$, $R^8$, X, m and n are as defined in claim 1 and $R^{12}$ is OH, Cl, Br, or a carboxylic acid moiety to form an anhydride;

or b) hydrolysis of a compound of formula (Ia)

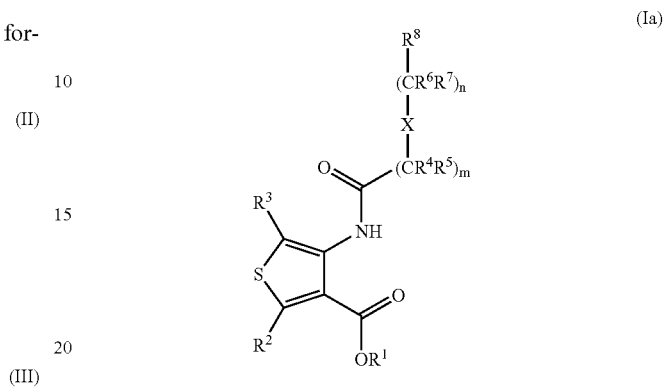

(Ia)

wherein $R^2$, $R^3$, $R^4$, $R^5$, $R^6$, $R^7$, $R^8$, X, m and n are as defined in claim 1 and $R^1$ is lower-alkyl.

26. A pharmaceutical composition, comprising a therapeutically effective amount of a compound according to claim 1 or 2-methyl-4-[[(phenylmethoxy)carbonyl]amino]-3-thiophenecarboxylic acid methyl ester, and a pharmaceutically acceptable carrier and/or adjuvant.

* * * * *